US010448962B2

(12) United States Patent
Dhindsa

(10) Patent No.: US 10,448,962 B2
(45) Date of Patent: *Oct. 22, 2019

(54) ENDOSCOPIC STONE-EXTRACTION DEVICE

(71) Applicant: INNON Holdings, LLC, Gilbert, AZ (US)

(72) Inventor: Avtar S. Dhindsa, Gilbert, AZ (US)

(73) Assignee: INNON Holdings, LLC, Gilbert, AZ (US)

( * ) Notice: Subject to any disclaimer, the term of this patent is extended or adjusted under 35 U.S.C. 154(b) by 263 days.

This patent is subject to a terminal disclaimer.

(21) Appl. No.: 15/601,610

(22) Filed: May 22, 2017

(65) Prior Publication Data

US 2017/0258481 A1    Sep. 14, 2017

Related U.S. Application Data

(63) Continuation-in-part of application No. 14/452,179, filed on Aug. 5, 2014, now Pat. No. 9,655,634.

(Continued)

(51) Int. Cl.
*A61B 17/221* (2006.01)
*A61B 1/00* (2006.01)
*A61B 1/307* (2006.01)

(52) U.S. Cl.
CPC ........ *A61B 17/221* (2013.01); *A61B 1/00087* (2013.01); *A61B 1/00085* (2013.01);
(Continued)

(58) Field of Classification Search
CPC .......... A61B 17/221; A61B 2017/2212; A61B 17/320016; A61B 17/32056;
(Continued)

(56) References Cited

U.S. PATENT DOCUMENTS 3,955,578 A    5/1976   Chamness et al.
4,557,255 A    12/1985  Goodman
(Continued)

FOREIGN PATENT DOCUMENTS

JP    2004-16668     1/2004
WO    WO 1992-16153  10/1992

OTHER PUBLICATIONS

European Search Report for EP 15807083 dated Dec. 14, 2017, 1 page.
(Continued)

*Primary Examiner* — Katherine M Shi
(74) *Attorney, Agent, or Firm* — Spencer Fane LLP; Steven J. Laureanti

(57) ABSTRACT

An endoscopic stone-extraction device is provided comprising a support filament comprising an end portion, a sheath comprising a lumen, wherein the support filament is disposed in the lumen such that the sheath is slideable with respect to the support filament, and a handle comprising an actuator. Movement of the actuator in a first direction retracts the sheath and causes a shape to expand outside the lumen. Movement of the actuator in a second direction advances the sheath and causes the shape to at least partially collapse inside the lumen. Other embodiments are provided, and any of these embodiments can be used alone or in combination.

16 Claims, 18 Drawing Sheets

Related U.S. Application Data

(60) Provisional application No. 62/011,367, filed on Jun. 12, 2014.

(52) U.S. Cl.
CPC ....... *A61B 1/307* (2013.01); *A61B 2017/2212* (2013.01); *A61B 2017/2215* (2013.01); *A61B 2017/2217* (2013.01)

(58) Field of Classification Search
CPC .. A61B 2017/0034; A61B 2017/00353; A61B 2017/00867; A61B 2017/2215; A61B 2017/2217
USPC ................................. 606/113, 127, 128, 200
See application file for complete search history.

(56) References Cited

U.S. PATENT DOCUMENTS

| | | |
|---|---|---|
| 4,590,938 A | 5/1986 | Segura |
| 4,612,931 A | 9/1986 | Dormia |
| 4,873,978 A | 10/1989 | Ginsburg |
| 4,927,426 A | 5/1990 | Dretler |
| 5,066,295 A | 11/1991 | Kozak et al. |
| 5,098,440 A | 3/1992 | Hillstead |
| 5,190,542 A | 3/1993 | Nakao et al. |
| 5,192,286 A | 3/1993 | Phan |
| 5,197,968 A | 3/1993 | Clement |
| 5,201,740 A | 4/1993 | Nakao et al. |
| 5,397,320 A | 3/1995 | Essig et al. |
| 5,417,697 A | 5/1995 | Wilk et al. |
| 5,423,805 A | 6/1995 | Brucker et al. |
| 5,496,330 A | 3/1996 | Bates et al. |
| 5,535,759 A | 7/1996 | Wilk |
| 5,788,710 A | 8/1998 | Bates |
| 5,814,097 A | 9/1998 | Sterman et al. |
| 5,910,154 A | 6/1999 | Tsugita et al. |
| 5,911,734 A | 6/1999 | Tsugita et al. |
| 5,957,932 A | 9/1999 | Bates |
| 5,989,266 A | 11/1999 | Foster |
| 5,993,474 A | 11/1999 | Ouchi |
| 6,007,546 A | 12/1999 | Snow et al. |
| 6,010,512 A | 1/2000 | Chu et al. |
| 6,015,415 A | 1/2000 | Avellent |
| 6,027,520 A | 2/2000 | Tsugita et al. |
| 6,042,598 A | 3/2000 | Tsugita et al. |
| 6,059,796 A | 5/2000 | Bilitz et al. |
| 6,077,274 A | 6/2000 | Ouchi |
| 6,093,196 A | 7/2000 | Okada |
| 6,096,053 A | 8/2000 | Bates |
| 6,099,534 A | 8/2000 | Bates |
| 6,165,179 A | 12/2000 | Cathcart et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,190,394 B1 | 2/2001 | Lind et al. |
| 6,216,044 B1 | 4/2001 | Kordis |
| 6,224,611 B1 | 5/2001 | Ouchi |
| 6,235,026 B1 | 5/2001 | Smith |
| 6,245,089 B1 | 6/2001 | Daniel et al. |
| 6,270,513 B1 | 8/2001 | Tsugita et al. |
| 6,280,451 B1 | 8/2001 | Bates et al. |
| 6,346,116 B1 | 2/2002 | Brooks et al. |
| 6,348,056 B1 | 2/2002 | Bates et al. |
| 6,416,519 B1 | 7/2002 | VanDusseldorp |
| 6,419,679 B1 | 7/2002 | Dhindsa |
| 6,494,885 B1 | 12/2002 | Dhindsa |
| 6,500,182 B2 | 12/2002 | Foster |
| 6,537,297 B2 | 3/2003 | Tsugita et al. |
| 6,551,327 B1 | 4/2003 | Dhindsa |
| 6,652,537 B2 | 11/2003 | Mercereau et al. |
| 6,673,080 B2 | 1/2004 | Reynolds et al. |
| 6,679,893 B1 | 1/2004 | Tran |
| 6,706,054 B2 | 3/2004 | Wessman et al. |
| 6,743,237 B2 | 6/2004 | Dhindsa |
| 6,752,811 B2 | 6/2004 | Chu et al. |
| 6,786,865 B2 | 9/2004 | Dhindsa |
| 7,041,116 B2 | 5/2006 | Goto et al. |
| 7,087,062 B2 | 8/2006 | Dhindsa |
| 7,169,154 B1 | 1/2007 | Que et al. |
| 7,282,055 B2 | 10/2007 | Tsuruta |
| 7,618,437 B2 | 11/2009 | Kakao |
| 7,753,919 B2 | 7/2010 | Kanamaru |
| 8,142,443 B2 | 3/2012 | Saleh |
| 8,142,445 B2 | 3/2012 | Teague |
| 8,206,401 B2 | 6/2012 | Nakao |
| 8,303,612 B2 | 11/2012 | Nakao et al. |
| 8,308,739 B2 | 11/2012 | Wolfe |
| 8,328,819 B2 | 12/2012 | Dilinger |
| 8,328,820 B2 | 12/2012 | Diamant et al. |
| 8,361,084 B2 | 1/2013 | Cheng et al. |
| 8,469,970 B2 | 6/2013 | Diamant |
| 8,732,933 B2 | 5/2014 | Que et al. |
| 8,828,022 B2 | 9/2014 | White et al. |
| 8,852,204 B2 | 10/2014 | Gordon |
| 8,974,469 B2 | 3/2015 | Taube et al. |
| 8,998,946 B2 | 4/2015 | Morero |
| 9,271,746 B2 | 3/2016 | Diamant et al. |
| 2004/0199048 A1 | 10/2004 | Clayman et al. |
| 2005/0004595 A1* | 1/2005 | Boyle ............... A61F 2/013 606/200 |
| 2006/0052798 A1 | 3/2006 | Kanamaru |
| 2006/0293697 A1 | 12/2006 | Nakao et al. |
| 2007/0118165 A1 | 5/2007 | DeMello et al. |
| 2007/0225730 A1 | 9/2007 | Deal |
| 2007/0299456 A1 | 12/2007 | Teague |
| 2008/0009884 A1 | 1/2008 | Kennedy |
| 2011/0106077 A1 | 5/2011 | Yanuma et al. |
| 2012/0029556 A1 | 2/2012 | Masters |
| 2014/0364868 A1 | 12/2014 | Dhindsa |
| 2015/0359548 A1* | 12/2015 | Dhindsa ............... A61B 17/221 606/127 |

OTHER PUBLICATIONS

International Search Report and Written Opinion for PCT/US2014/037693 dated Oct. 8, 2014, 9 pages.
Brochure, "Escape® Nitinol Stone Retrieval Basket", Boston Scientific Corporation, 2009, 2 pages.
Brochure, "Pietrow, MD, P., Stone Cone TM Nitinol Retrieval Coil Technique", Boston Scientific Corporation, 2004, 4 pages.
Dialog Abstract, Binmoeller, K, et al., "Endoscopic Management of Bile Ducts", Journal of Clinical Gastroenterology, vol. 32, No. 2 pp. 106-118, Dialog File No. 144, Accession No. 14957807.
Desai, et al., "The Dretler Stone Cone: A Device to Prevent Ureteral Stone Migration—The Clinical Experience", The Journal of Urology, vol. 167, May 2002, pp. 1985-1988.
"OXO Good Grips Dough Blender with Blades" printed on Jul. 25, 2013 from http://www.amazon.com/OXO-Grips-Dough-Blender-Blades/dp/B000QJE48O, pp. 1-6.
Picture, "omniFORCE TM Laser Stone Cage", printed on Jun. 10, 2013 from http://www.omnitechsystems.com/images/StoneCage.jpg, 1 pages.
NTrap® Stone Entrapment and Extraction Device, printed on Jul. 25, 2013 from https://www.cookmedical.com/product/-/catalog/display?ds=uro_ntrap_webds, 1 page.
International Search Report dated Nov. 12, 2015 for PCT/US2015/032750.

* cited by examiner

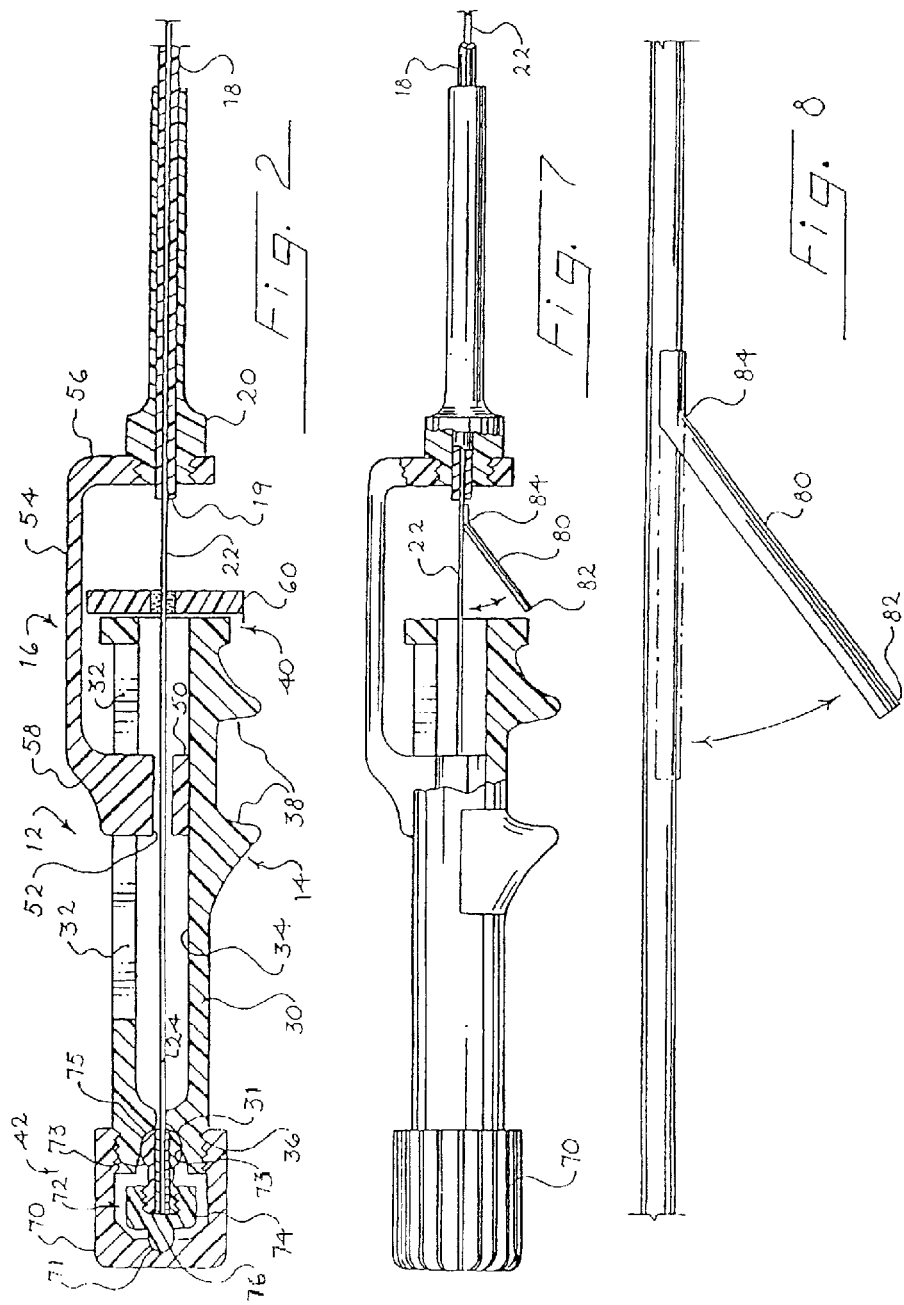

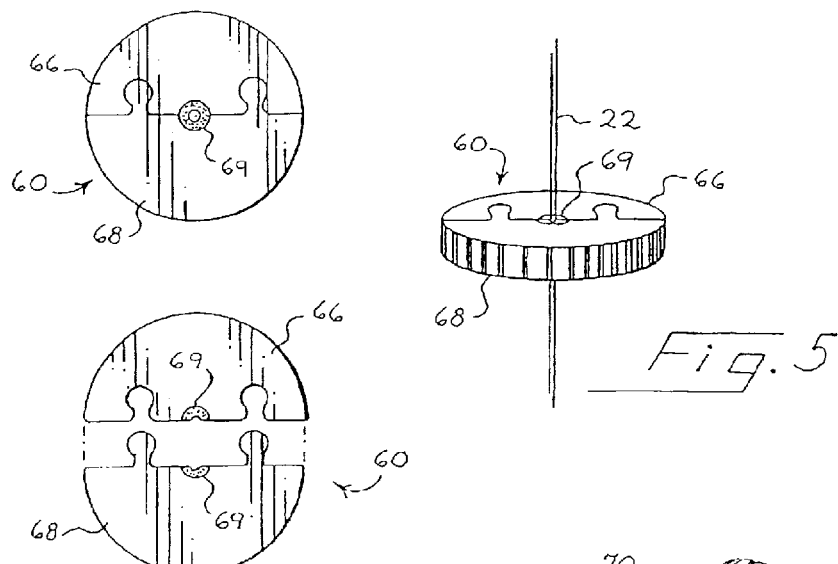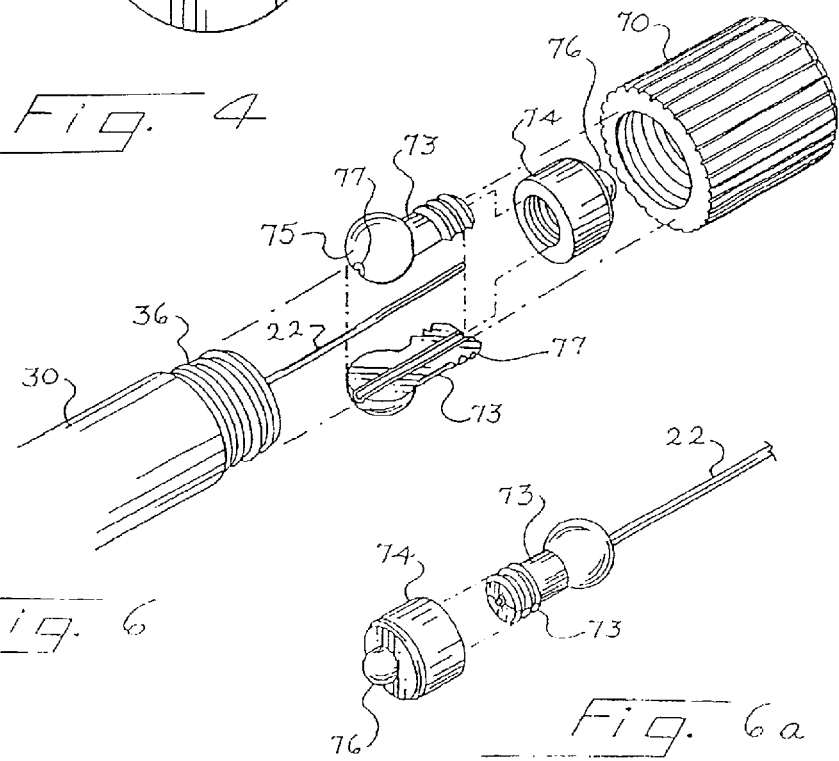

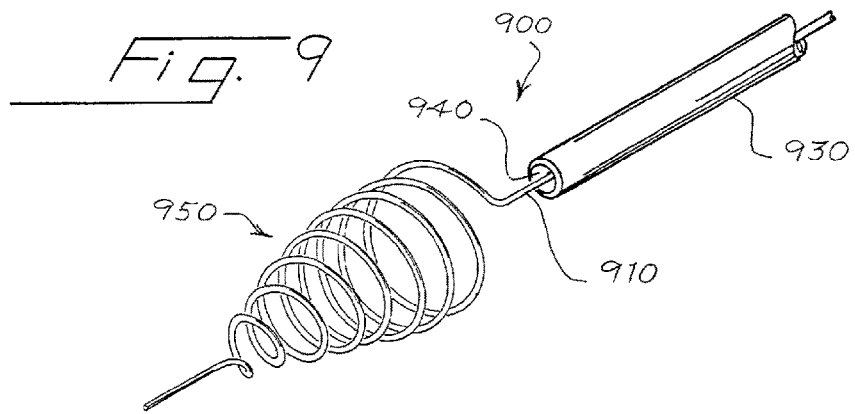
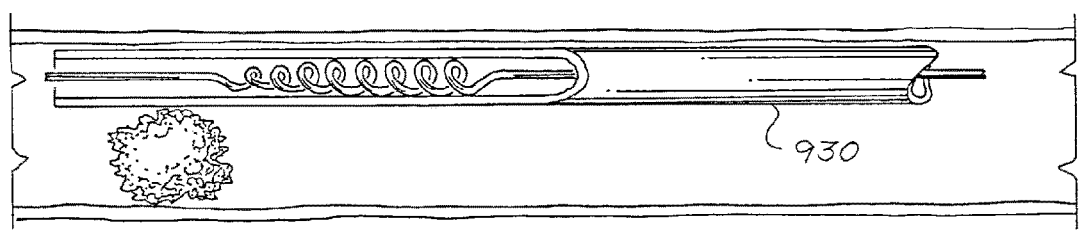
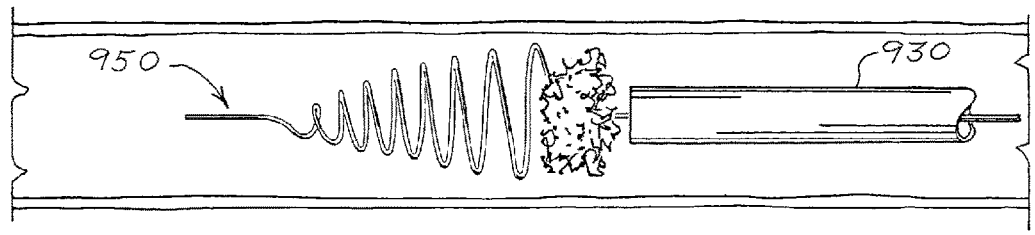
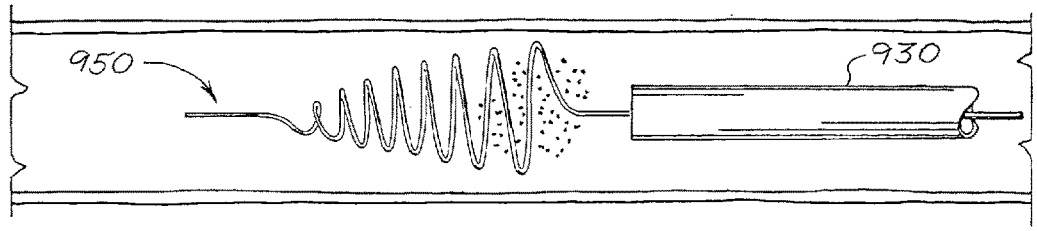

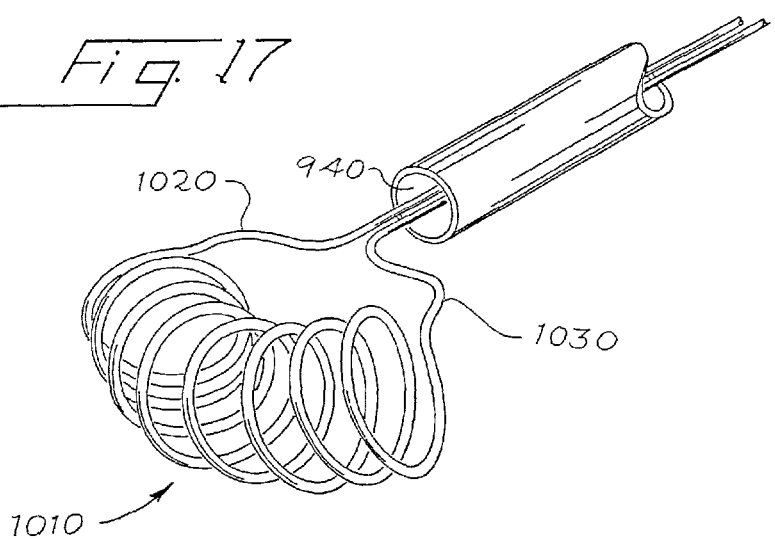
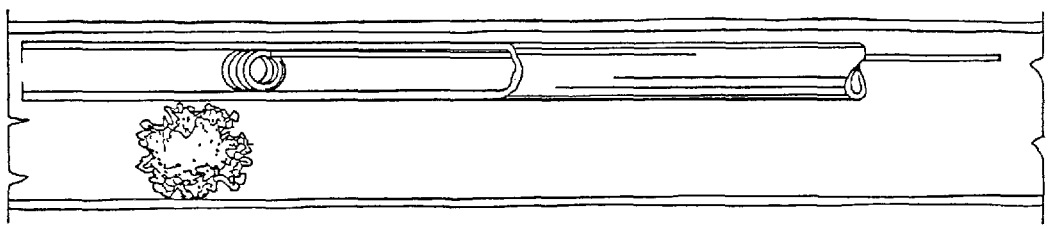
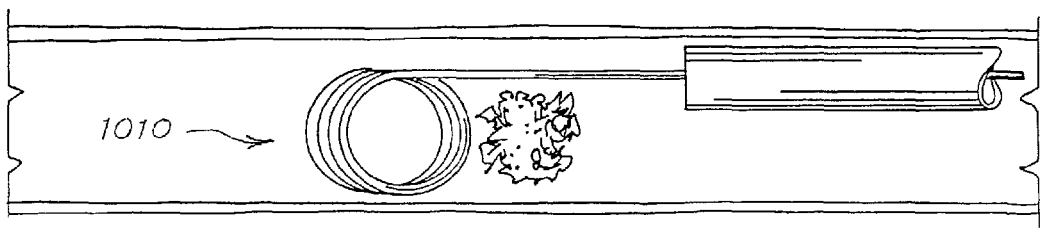
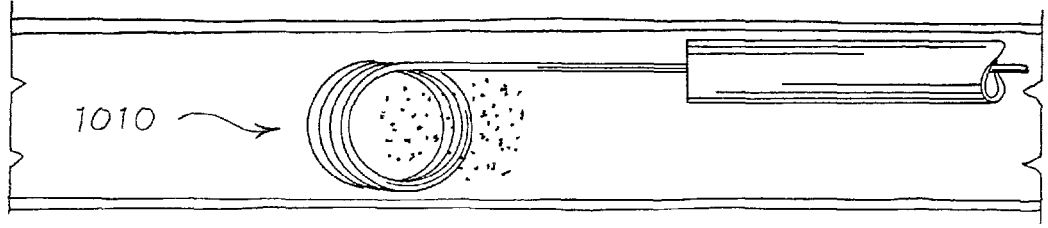

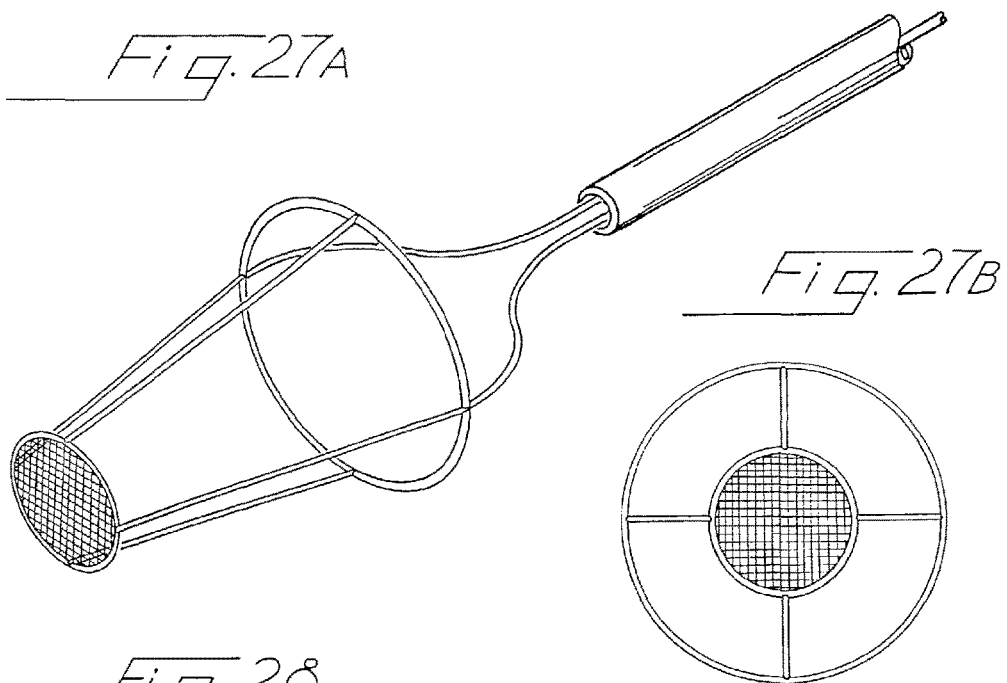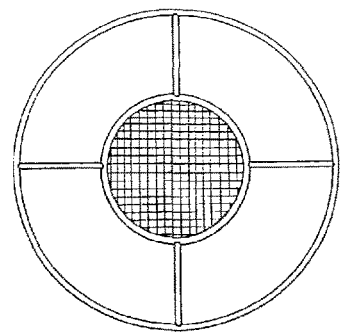
Fig. 27A
Fig. 27B
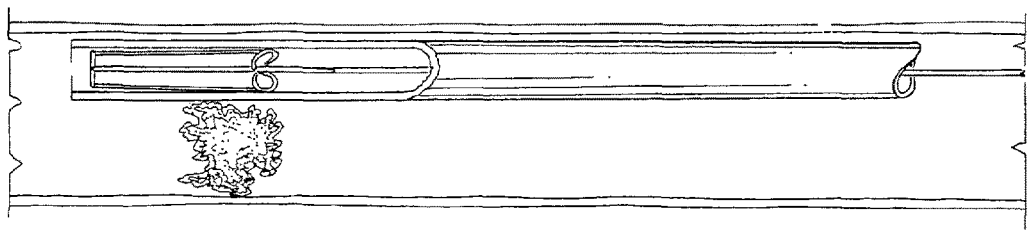
Fig. 28
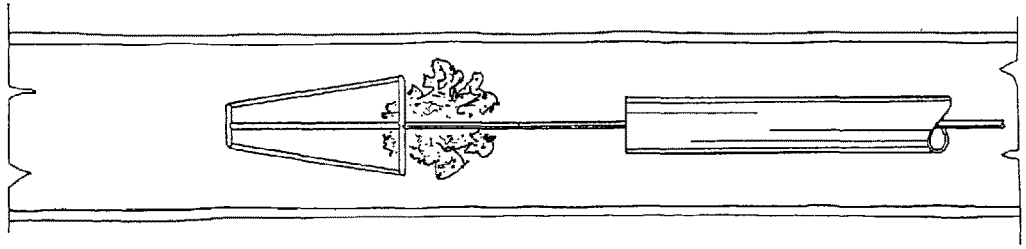
Fig. 29
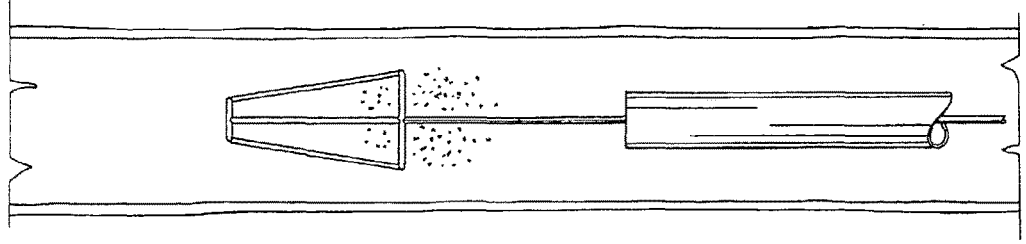
Fig. 30

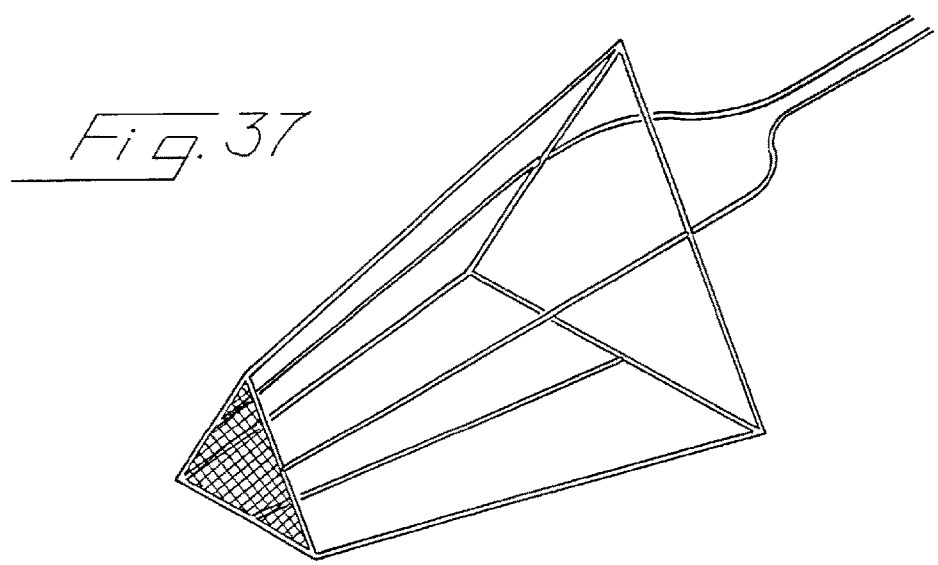
Fig. 37
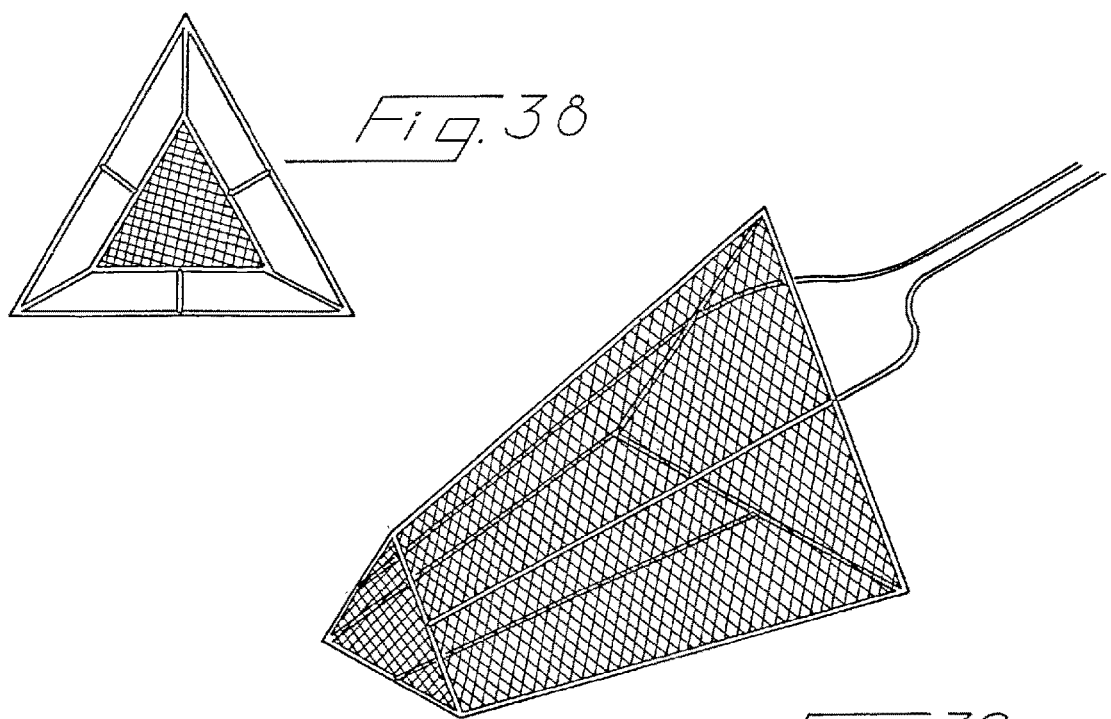
Fig. 38
Fig. 39
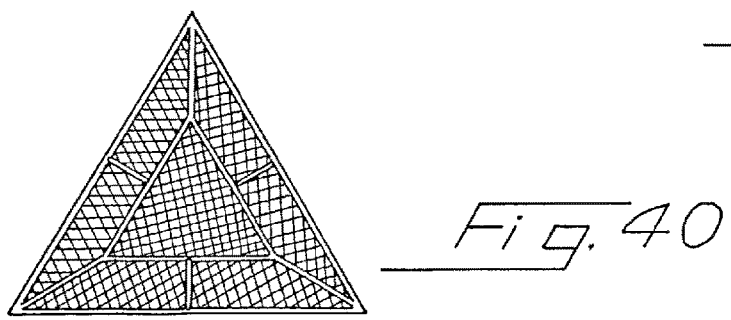
Fig. 40

ENDOSCOPIC STONE-EXTRACTION DEVICE

CROSS-REFERENCE TO RELATED APPLICATIONS

This application is a continuation-in-part of U.S. patent application Ser. No. 14/452,179, filed on Aug. 5, 2014, entitled "Endoscopic Stone-Extraction Device," which claims the benefit under 35 U.S.C. § 119(e) to U.S. Provisional Application No. 62/011,367, filed Jun. 12, 2014, and entitled "Endoscopic Stone-Extraction Device." U.S. patent application Ser. No. 14/452,179 and U.S. Provisional Application No. 62/011,367 are assigned to the assignee of the present application. The subject matter disclosed in U.S. patent application Ser. No. 14/452,179 and U.S. Provisional Application No. 62/011,367 is hereby incorporated by reference into the present disclosure as if fully set forth herein.

BACKGROUND

Basket-type devices have been used for extracting stones such as ureteral stones, calyceal stones and other calculi and the like from the renal or biliary systems. Various types of stone extraction baskets have been used in the past to extract stones and stone fragments (or other debris) from various biological systems. A typical stone extraction basket includes a wire basket carried by one end of a wire that is received within the lumen of a sheath. The end of the wire opposite the basket is secured to a handle that is used to slide the sheath over the wire, thereby moving the basket into and out of the lumen of the sheath. When the basket is out of the sheath, it expands to receive a stone. The sheath is then moved toward the basket to reduce the size of the basket openings, and the basket and the enclosed stone are removed from the body. Ultrasonic, laser, and electro-hydraulic techniques have been used to fragment stones in situ. Typically, the stone fragments are left in the body to be excreted or can be attempted to be removed with a stone extraction basket or the like.

BRIEF DESCRIPTION OF THE DRAWINGS

FIG. 2 illustrates a cross-sectional view taken along line 2-2 of FIG. 1;

FIGS. 3, 4 and 5 illustrate detailed views of a thumb wheel included in the embodiment of FIGS. 1 and 2;

FIG. 6 illustrates an exploded perspective view of a portion of the handle and the end portion of the wire of the embodiment of FIGS. 1 and 2;

FIG. 6A illustrates an exploded perspective view of the elements 73, 74 of FIG. 6 from another viewing angle;

FIG. 7 illustrates a cross-sectional view corresponding to that of FIG. 2 of another embodiment;

FIG. 8 illustrates a fragmentary side view of selected elements of the embodiment of FIG. 7;

FIGS. 9-12 illustrate an endoscopic stone-extraction device of an embodiment having a tapered corkscrew shape;

FIGS. 17-20 illustrate an endoscopic stone-extraction device of an embodiment having an arced corkscrew shape;

FIGS. 27A-30 illustrate an endoscopic stone-extraction device of an embodiment having an open basket, circular shape;

FIGS. 37-40 illustrate an endoscopic stone-extraction device of an embodiment having an open and closed basket, triangular shapes;

DETAILED DESCRIPTION

Introduction

Figures 48, 49:
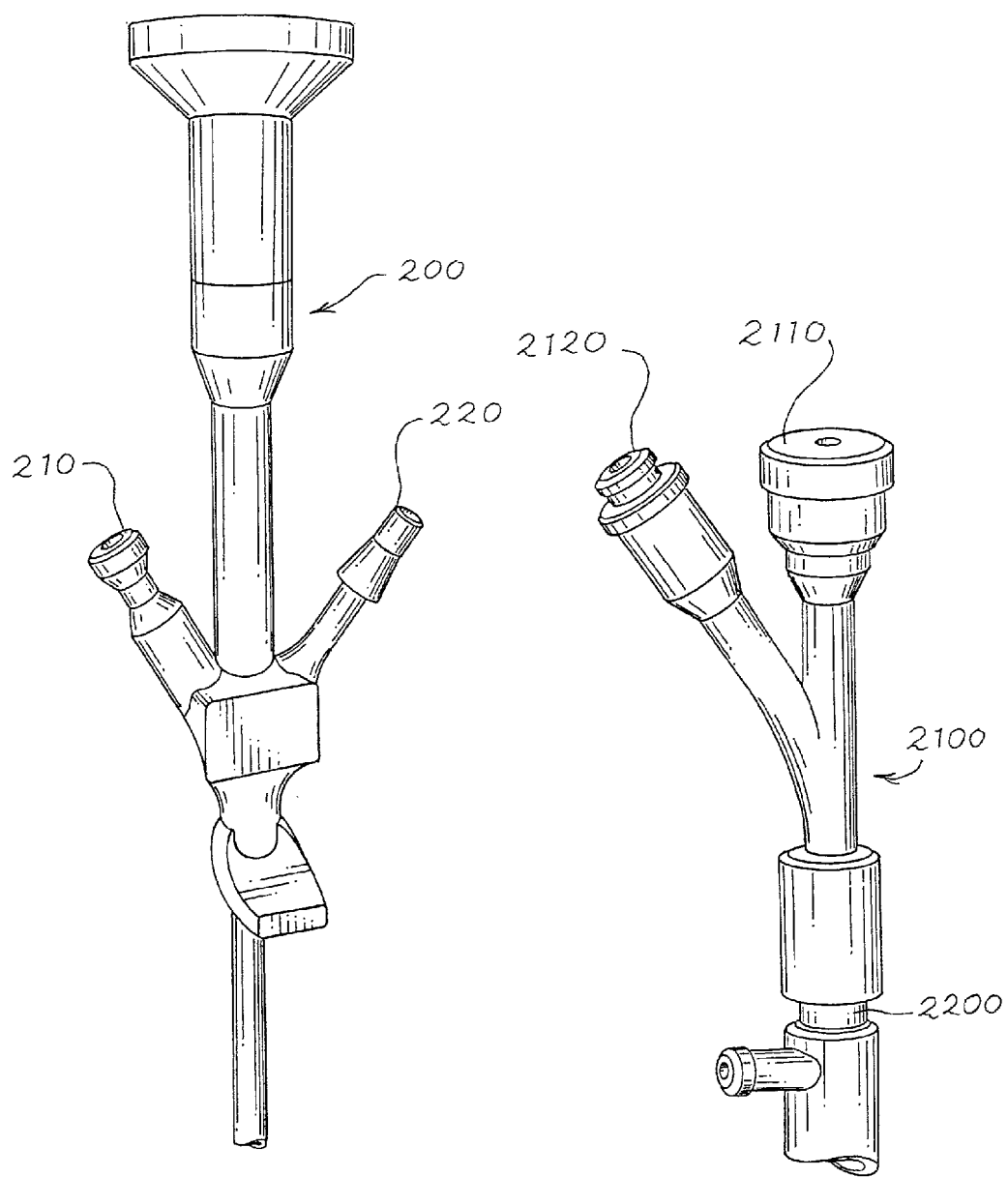
FIG. 48 illustrates a two-port endoscope that can be used with an endoscopic stone-extraction device of an embodiment.
FIG. 49 illustrates a Y-adapter that can be used with the two-port endoscope of FIG. 48.

In a stone-removal procedure, an endoscope (e.g., a ureteroscope) is inserted into the body, with the distal end of the scope near the stone to be extracted. As shown in FIG. 48, an endoscope 200 typically has two ports 210, 220. One of the ports 210 is typically used as an irrigation port (for saline to be introduced into the extraction site), and the second port 220 is used for various instruments. In some situations, the second port 220 is initially used for the sheath that holds a stone extraction basket (however, other situations are possible, as will be discussed below).

The procedure begins with inserting the endoscope into the body (e.g., inserting the ureteroscope into the ureter) and identifying and locating the stone. Once the stone is identified, a decision is made whether the stone can be extracted out intact or whether the stone needs to be fragmented because it is too large to be extracted out. There are several technologies that are available for fragmentation, and a popular and effective technology is a laser. One of the problems faced during fragmentation is retropulsion, whereby the stone migrates up the ureter towards the kidney. Retropulsion makes the procedure more difficult and is associated with more complications.

To prevent migration of the stone, a mechanical device can be used as a trapping/backstop device to the stone. When a mechanical trapping/backstop device is used, the scope is inserted, the stone is identified, and the mechanical trapping/backstop device is inserted through one of the ports of the scope (the other port is used as an irrigation channel). The mechanical trapping/backstop device is then placed beyond the stone and deployed. Since a two-port scope does not have any other access point for the laser fiber, the mechanical trapping/backstop is left in the body, while the ureteroscope is removed from the body and then reinserted. The stone is identified again, and the laser fiber is then inserted into the open port to fragment the stone. The fragmented stone can be left inside the ureter to be passed out or can be dragged into the bladder and then extracted out either by irrigation or by using a stone basket (the mechanical trapping/backstop device usually is not very effective at extracting stone fragments, which is why the separate stone basket is used).

Instead of using a mechanical trapping/backstop device, a gel can be inserted into the body just beyond the stone, which acts as a trap and/or a backstop to the stone. After the stone fragments have been removed, the physician introduces cold saline into the ureter, which dissolves the jelly so it can drain out of the ureter. As another alternative to using a mechanical trapping/backstop device, a standard stone basket can be used to engage the stone. Once the stone is engaged, the basket filament and sheath are cut at the handle and the basket with the stone inside are left inside the body. The sheath is removed along with the ureteroscope. The procedure is carried out as mentioned above. However, some stone baskets, such as a four-wire basket, may not serve as an effective trapping/backstop since stone fragments can escape from the sides of the basket.

There are several difficulties associated with the current procedure. First, it is a multistep process, requiring the scope to be removed and re-inserted into the patient multiple times. Second, when a mechanical trapping/backstop device is used, it may not stay in place when the scope is removed and reinserted into the body (e.g., the trapping/backstop device can move up or down the ureter and sometimes into the kidney or come out in front of the stone instead of staying behind the stone). Third, stone fragments can escape around the trapping/backstop device (or a stone basket when a separate trapping/backstop device is not used) because these devices do not completely occlude the lumen.

The following endoscopic stone-extraction devices can function both as a trapping/backstop device and a stone extraction device, which eliminates at least one of the steps in the multi-step process described above.

According to embodiments, aspects of the following stone baskets reduce drawbacks associated with "dusting" techniques of stone removal. Dusting comprises pulverizing a stone into extremely fine fragments by using, for example, low energy, high frequency laser pulses from programmable holmium lasers. These lasers allow configuring the energy level, pulse rate, and power of the laser to safely fragment or dust a stone of various compositions, hardnesses, locations within the body, or other considerations. For example, a low-energy laser dusting setting may comprise an energy level of 0.2 Joules and a pulse rate of 50 hertz, for a total power of 10 Watts. Soft stones are often dusted completely using this or similar laser dusting settings. For harder stones (for example, those comprising Calcium Oxalate Monohydrate), the laser may be adjusted to a higher energy level and a lower pulse rate, such as, for example, an energy level of 0.5 Joules and a pulse rate of 20 Hertz, for a total power of 10 Watts. Some stones, however, comprise soft shells covering harder cores. To remove these stones, the soft shell is eliminated by using the dusting technique with a low-energy laser dusting setting. When the harder core is exposed, the laser settings are adjusted to a higher energy level to continue breaking up the core of the stone. If the core is exceptionally hard, the technique may require first breaking the core into fragments prior to dusting. This technique may be referred to as a "popcorn" technique and may comprise, for example, placing the laser fiber in the middle of a cluster of stone fragments (such as, for example, those from a fragmented core) and firing the laser. The fragments from the cluster begin to "popcorn" around the laser fiber and break into smaller fragments or into dust.

Dusting a stone is best accomplished when first directing the laser energy to the edges of the stone. However, the extremely fine dust and fragments of the stone quickly cloud the visibility from the ureteroscope, which limits the physician's ability to continue viewing the stone and to correctly orient the laser.

Exemplary Endoscopic Stone-Extraction Devices

FIGS. 9-44 illustrate endoscopic stone-extraction devices of several embodiments. Turning first to FIG. 9, the endoscopic stone-extraction device 900 in this embodiment has a support filament 910 comprising an end portion and a sheath 930 comprising a lumen 940, wherein the support filament 910 is disposed in the lumen 940 such that the sheath 930 is slideable with respect to the support filament 910. A handle 1700 (see FIG. 45) comprises an actuator 1710. (Any type of handle with an actuator can be used, and other examples of handles are provided below. Details of any particular handle design (discussed herein or otherwise) should not be read into the claims unless explicitly recited therein). Movement of the actuator 1710 in a first direction retracts the sheath 930 and causes the end portion to expand outside the lumen in a corkscrew shape 950. Movement of the actuator in a second direction advances the sheath 930 and causes the corkscrew shape 950 to at least partially collapse inside the lumen 940. FIGS. 10-12 show how the endoscopic stone-extraction device can be deployed to hold a stone in place before destruction and collect the stone fragments after destruction.

In this embodiment, the corkscrew shape 950 is a conical-corkscrew shape that tapers from a larger portion closer to the lumen 940 to a smaller portion farther away from the lumen 940. However, other configurations are possible. For example, FIGS. 13-16 show a non-tapered corkscrew shape 1000, and FIGS. 17-20 show a corkscrew shape 1010 that is arced in a direction generally perpendicular to an axis of the lumen 940, wherein the corkscrew shape 1010 is connected to the support filament via a plurality of secondary filaments 1020, 1030.

In another embodiment (shown in FIGS. 21-24), movement of the actuator in a first direction retracts the sheath and causes the end portion to expand outside the lumen in a rake shape 1050, wherein the rake shape 1050 is connected to the support filament via a plurality of secondary filaments 1060, 1070. The rake shape can have pointed prongs 1080 (as in FIG. 21) or rounded prongs 1090 (as in FIGS. 25 and 26).

In yet another embodiment (shown in FIGS. 31 and 32), movement of the actuator in a first direction retracts the sheath and causes the end portion to expand outside the lumen in a basket shape 2000 that tapers from a larger portion 2010 closer to the lumen to a smaller portion 2020 farther away from the lumen, wherein the larger portion 2010 is an opening of the basket shape 2000, and the smaller portion 2020 is meshed. The basket shape 2000 is connected to the support filament via a plurality of secondary filaments 2030, 2040, and the larger and smaller portions 2010, 2020 are joined together by an additional plurality of filaments 2050, 2060. The sides of the basket shape can be meshed (as in FIGS. 31 and 32) or open (as in FIGS. 27A-30). Also, the smaller and larger portions can take any suitable shape, such as circular (as in FIGS. 27A-32), rectangular/square (as in FIGS. 33-36), or triangular (as in FIGS. 37-40). Of course, other shapes can be used.

In yet another embodiment, movement of the actuator in a first direction retracts the sheath and causes the end portion to expand outside the lumen in a two-dimensional mesh shape 2500 (see FIGS. 41-44) that is generally perpendicular to an axis of the lumen, wherein the two-dimensional mesh shape 2500 is connected to the support filament via a plurality of secondary filaments 2510, 2520. The two-dimensional mesh shape 2500 can take any suitable shape, such as a square (as in FIG. 41) or other shapes, such as, for example, a circle (as in FIGS. 50-53), triangle (as in FIGS. 54-56), a polygon, or any other suitable shape, according to particular needs.

Figure 41:
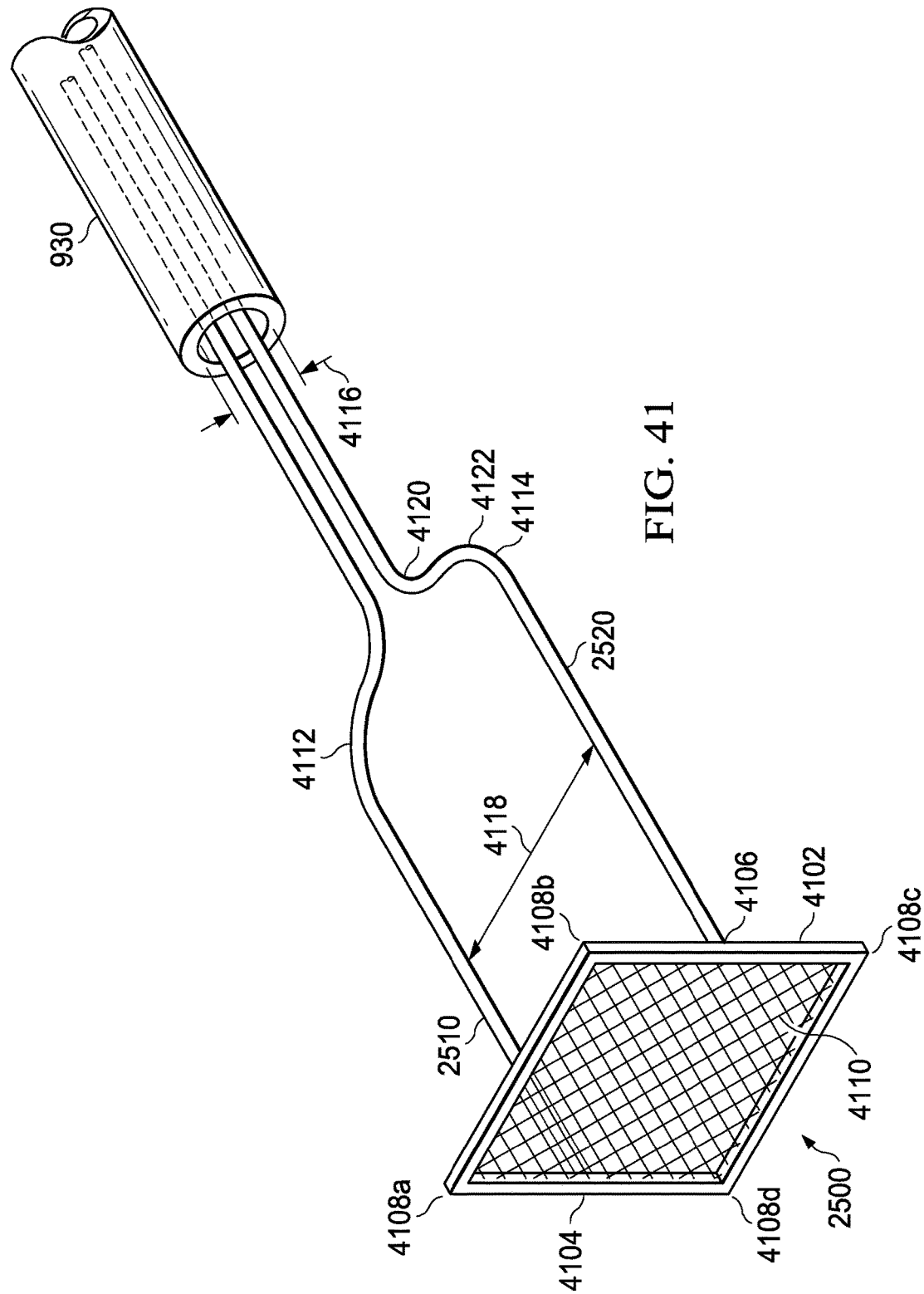
FIGS. 41-44 illustrate an endoscopic stone-extraction device of an embodiment having a two-dimensional mesh shape.

FIG. 41 illustrates a two-dimensional mesh shape 2500 when the two-dimensional mesh shape is a square, according to an embodiment. Two-dimensional mesh shape 2500 comprises two secondary filaments 2510, 2520 coupled to rim 4102 at attachment points 4104, 4106. According to embodiments, secondary filaments 2510, 2520 are coupled to attachment points 4104, 4106 at opposite sides of rim 4102, with attachment point 4104 between corners 4108a and 4108d and attachment point 4106 between corners 4108b-4108c.

Rim 4102 of two-dimensional mesh shape 2500 couples with mesh 4110, which comprises overlapping or interlaced strands to create a surface that is selectively porous to fragments of a stone based on size. According to embodiments, mesh 4110 comprises strands in a first direction (referred to as horizontal strands) perpendicular to strands in a second direction (referred to as vertical strands), with a horizontal spacing between adjacent horizontal strands and a vertical spacing between adjacent vertical strands. Horizontal spacing may be the same as, or different from, the vertical spacing depending on particular needs. According to some embodiments, mesh 4110 comprises only horizontal or only vertical strands. According to other embodiments, instead of being perpendicular, horizontal strands may be situated at any angle from vertical strands (such as, for example, 20, 30, 45, 50, 60, 70, 90, or any suitable number of degrees) that form quadrilateral or parallelogram openings of substantial uniformity that are repeated across at least fifty percent (and up to one hundred percent) of the surface of mesh 4110.

The spacing between adjacent strands determines the size of stone fragments that may pass through mesh 4110. For example, when the spacing between adjacent strands is two millimeters, stone fragments larger than two millimeters will be blocked from passing through mesh 4110. Although the spacing between adjacent strands is described as two millimeters, embodiments contemplate any suitable number or spacing of strands in mesh 4110, according to particular needs. Additionally, although strands in mesh 4110 are illustrated as overlapping or interlaced perpendicular strands, according to some embodiments, mesh 4110 comprises a net, wherein the net comprises strands that are twisted or wrapped to form openings in mesh 4110. According to other embodiments, mesh 4110 is formed by cutting a solid sheet of material by using, for example, a laser cutter or other tool, to form openings in mesh 4016. Although particular types of meshes are described, embodiments contemplate any suitable mesh 4106, according to particular needs.

According to some embodiments, rim 4102 is formed from an element separate from secondary filaments 2510, 2520 and/or mesh 4110, such as a filament, strand, or strip or other component that forms the outer edge or two-dimensional mesh shape 2500. According to embodiments, rim 4102 may comprise a softer material than secondary filaments 2510, 2520 and/or mesh 4110. According to other embodiments, rim 4102 is not separable from secondary filaments 2510, 2520 and/or mesh 4110 by being formed directly from, for example, overlapped, interlaced, or twisted filaments or fibers from secondary filaments 2510, 2520 and/or mesh 4110. According to some embodiments, secondary filaments 2510, 2520 couples directly to edges of mesh 4110.

Rim 4102 comprises attachment points 4104, 4106 that couple rim 4102 to secondary filaments 2510, 2520. Although attachment points 4104, 4106 may be located in any number on any location along rim 4102, as described in more detail below, particular locations have advantages over other locations.

Secondary filaments 2510, 2520 comprise hips 4112, 4114. Hips 4112, 4114 comprise the portion of secondary filaments 2510, 2520 which affect the opening and closing of the two-dimensional mesh shape 2500 by the pressure of the sheath 930 against the sides of hips 4112, 4114. For example, according to some embodiments, hips 4112, 4114 define the transition from first distance 4116 of the secondary filaments 2510, 2520 to second distance 4118 of the secondary filaments 2510, 2520, wherein first distance 4116 is equal to the inner diameter of the distal end of sheath 930, and second distance 4118 is equal to the distance between attachment points 4108, 4110, when two-dimensional mesh shape 2500 is fully deployed. Hips 4112, 4114 may comprise none, one, or any number of bends that transition the secondary filaments 2510, 2520 from first distance 4116 to second distance 4118. According to some embodiments, hips 4112, 4114 comprise a taper comprising a constant slope from first distance 4116 to second distance 4118. According to other embodiments, hips 4112, 4114 comprise an S or sigmoid curve comprising an outside curve 4120 proximal to sheath 930 and an inside curve 4122 proximal to the two-dimensional mesh shape 2500. The combination of the slope of the outside curve 4120 and the slope of the inside curve 4122 with the length of the hip 4112, 4114 over which the slope is defined controls the rate of the opening and closing of two-dimensional mesh shape 2500 in response to the movement of sheath 930. According to embodiments, outside curve 4120 and inside curve 4122 are proportional to the length of hips 4112, 4114 and/or secondary filaments 2510, 2520. For example, sudden movements of the basket when deploying near a stone may dislodge the stone and complicate the procedure. By forming hips 4112, 4114 such that hips 4112, 4114 curve outward from the center of sheath 930 by, for example, forming outside curve 4120 as an arc with a gradual change allows basket to open more slowly in response to the pressure from the sheath 930.

Hips 4112, 4114 of filaments 2510, 2520 may be configured, in combination with programming of the properties of rim 4102 and/or mesh 4110, so that the two-dimensional mesh shape 2500 closes inwardly or outwardly, such as in, a convex or concave shape. For example, according to some embodiments, rim 4102 may comprise a rigidity that varies along the circumference of the rim 4102. According to embodiments, rim 4102 may comprise a rigidity that increases or decreases from attachment points 4104, 4106. Based on the rigidity, two-dimensional mesh shape 2500 may be configured to close or open in response to movement of sheath 930 by folding substantially along a vertical or horizontal axis that bisects the two-dimensional mesh shape 2500, such as, for example, the axis formed from connection points 4104, 4106, or the axis perpendicular to it.

To further illustrate operation of two-dimensional mesh shape 2500, an example is now given. In the following example, two-dimensional mesh shape 2500 comprises a shape memory material, such as a shape memory metal, connected to the support filament via secondary filaments 2510, 2520. When two-dimensional mesh shape 2500 is a square, secondary filaments 2510, 2520 may be attached at attachment points 4104, 4106 of two-dimensional mesh shape 2500 on opposite sides of rim 4102, with attachment point 4104 between corners 4108a and 4108d and attachment point 4106 between corners 4108b-4108c. In response to the movement of the actuator, as outlined herein, sheath 930 advances and causes two-dimensional mesh shape 2500 to partially collapse inside lumen of sheath 930.

Figure 42:
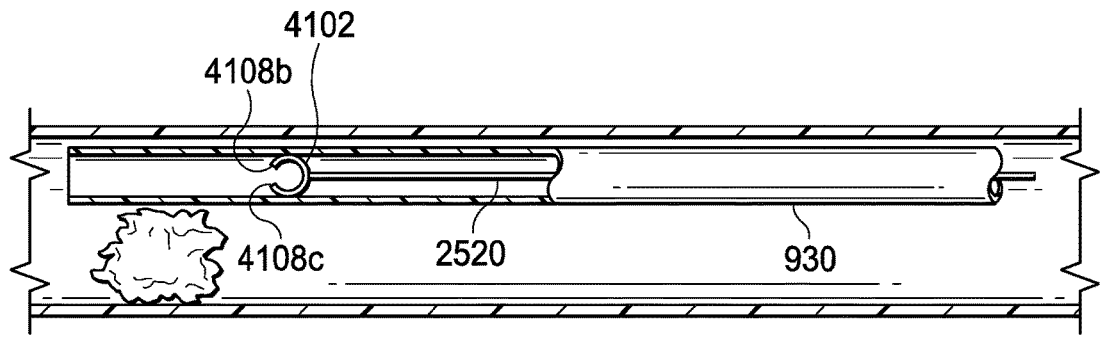

FIG. 42 illustrates two-dimensional mesh shape 2500 collapsed in an inverted C-shape inside the lumen of sheath 930, according to an embodiment. Two-dimensional mesh shape 2500 may at least partially collapse in an inverted C-shape inside the lumen of sheath 930 in response to the advancing of sheath 930.

According to embodiments, using exactly two secondary filaments 2510, 2520 achieves the illustrated C-shape of two-dimensional mesh shape 2500 when two-dimensional mesh shape 2500 partially collapses inside the lumen of sheath 930. The collapsing of two-dimensional mesh shape 2500 is caused by a force that is translated from the pressure of sheath 930 pressing against secondary filaments 2510, 2520 as sheath 930 advances along the length of the secondary filaments 2510, 2520. By attaching exactly two secondary filaments 2510, 2520, each on opposite sides of two-dimensional mesh shape 2500 between corners 4108a-4108d, two-dimensional mesh shape 2500 is free to collapse in a C-shape without being restricted by additional secondary filaments.

Two-dimensional mesh shape 2500 made from memory material causes two-dimensional mesh shape 2500 to collapse in a particular form based on the pressure from sheath 930 against the sides of hips 4112, 4114.

Using exactly two secondary filaments 2510, 2520 attached at attachment points 4104, 4106 (with attachment point 4104 between corners 4108a and 4108d and attachment point 4106 between corners 4108b-4108c) on two opposite sides of two-dimensional mesh shape 2500 allows forming the C-shape of two-dimensional mesh shape 2500, reduces the size of the endoscopic stone-extraction device and the width of two-dimensional mesh shape 2500 for a given surface area, and allows precise control of the deployed size while trapping a stone and preventing stone migration.

Figure 43:
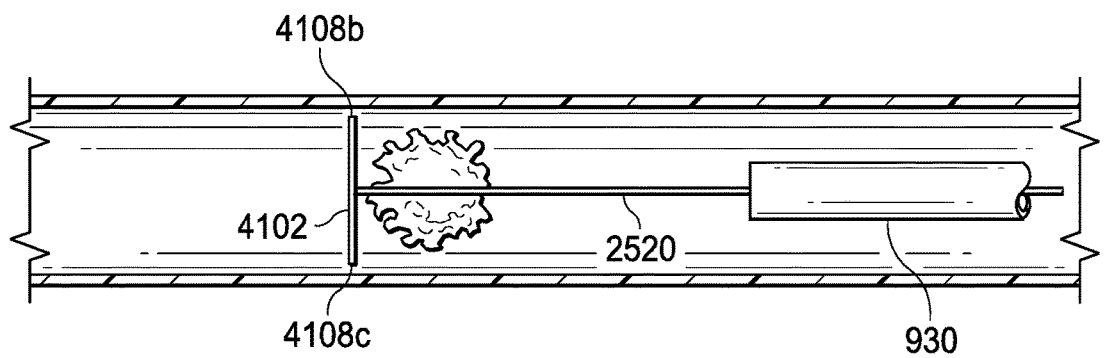

FIG. 43 illustrates two-dimensional mesh shape 2500 deployed behind a stone, according to an embodiment. When sheath 930 is retracted, two-dimensional mesh shape 2500 opens to form a trapping/backstop device and stone-capture device to allow the stone to be broken up without large fragments being allowed to migrate further up the lumen.

Figure 44:
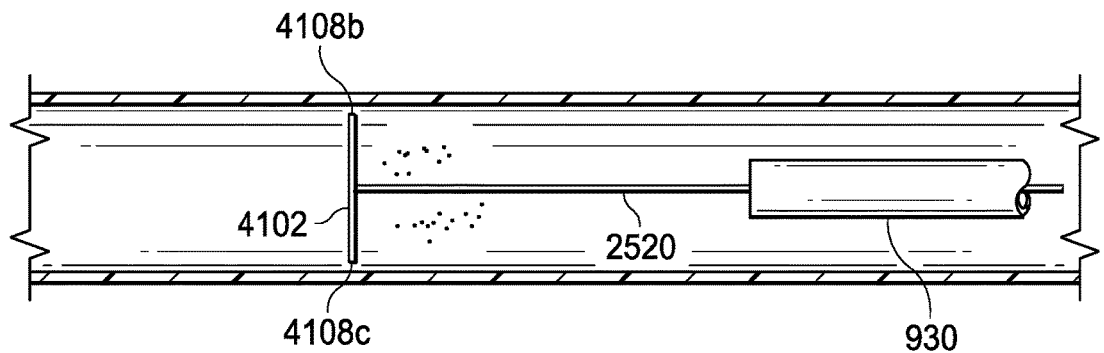
Figure 45:
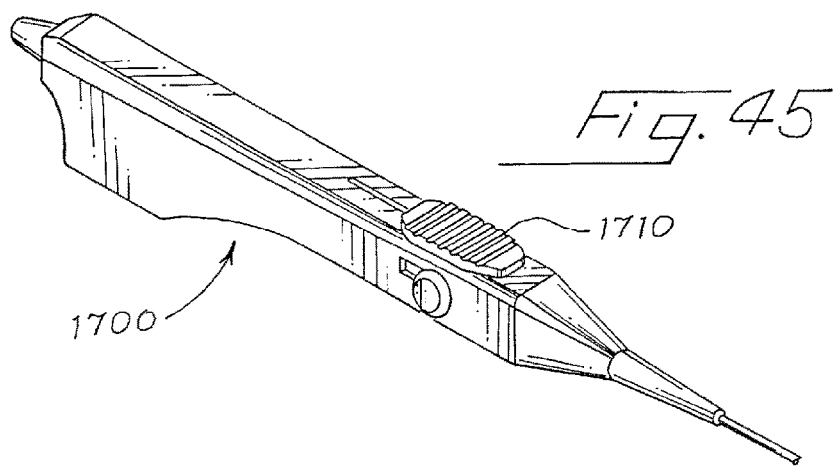
FIG. 45 illustrates a handle of an endoscopic stone-extraction device of an embodiment.

FIG. 44 illustrates two-dimensional mesh shape 2500 deployed behind fragments of a stone, according to an embodiment. After the stone is fragmented, such as by a laser, two-dimensional mesh shape 2500 captures fragments of the stone to prevent migration up the lumen. Two-dimensional mesh shape 2500 may then be closed by advancing the sheath, thereby capturing most or all of the fragments for removal from the lumen.

The diameter of a ureter and the diameter of an endoscope's working channel are limited, but, at the same time, it is useful to have a large surface area expanded inside the ureter to serve as a mechanical trapping/backstop device (such as to prevent stone migration during stone removal or stone breakup by a laser) or for capturing a stone. Attaching between corners 4108a-4108d on opposite sides, as opposed to attaching at corners 4108a-4108d, of two-dimensional square shape 2500 allows a given surface area to be deployed inside the ureter with a reduced distance between the attachment points 4104, 4106 of secondary filaments 2510, 2520 and therefore a reduced width of two-dimensional mesh shape 2500. This allows a larger surface area to be deployed inside a ureter or endoscope of a given diameter. For example, for a two-dimensional mesh shape 2500 of a given surface area, attaching secondary filaments 2510, 2520 on opposite sides at the midpoints between corners 4108a-4108d, as opposed to at corners 4108a-4108d, of two-dimensional mesh shape 2500, when the shape is a square, reduces the distance between the attachment points 4104, 4106 of secondary filaments 2510, 2520 and the width of the two-dimensional square shape by up to approximately 29%. Adding more than two secondary filaments 2510, 2520 would increase the space taken up by secondary filaments 2510, 2520 when deployed beyond that achieved with exactly two secondary filaments 2510, 2520. This may reduce the possible surface area of two-dimensional mesh shape 2500 that would fit into a ureter or working channel of an endoscope of a particular diameter.

As discussed above, using exactly two secondary filaments 2510, 2520 provides control and collapsing of two-dimensional mesh shape 2500 while preventing secondary filaments 2510, 2520 from being impeded by a stone to be removed by the endoscopic stone-extraction device. The collapse of two-dimensional mesh shape 2500 is controlled by the memory of the material forming two-dimensional mesh shape 2500 and the force translated from the pressure of sheath 930 against hips 4112, 4114 of secondary filaments 2510, 2520. To provide a backstop, to trap a stone, or to capture a stone within two-dimensional mesh shape 2500 requires precise control over the shape and size of the deployed portion of two-dimensional mesh shape 2500. Additionally, using two secondary filaments 2510, 2520 allows for precise control while eliminating all other secondary filaments that could dislodge or move a stone from being trapped, backstopped, or captured by two-dimensional mesh shape 2500. Although the mesh shape is discussed as comprising a shape memory material, any suitable material or combination of materials may be used, such as, for example, metal, polymer, composites, resin, rubber, or the like, including any of the foregoing, alone or in combination, programmed with shape memory As discussed above, two-dimensional mesh shape 2500 may comprise shapes additional to a square-shaped two-dimensional mesh shape 2500.

Figure 50:
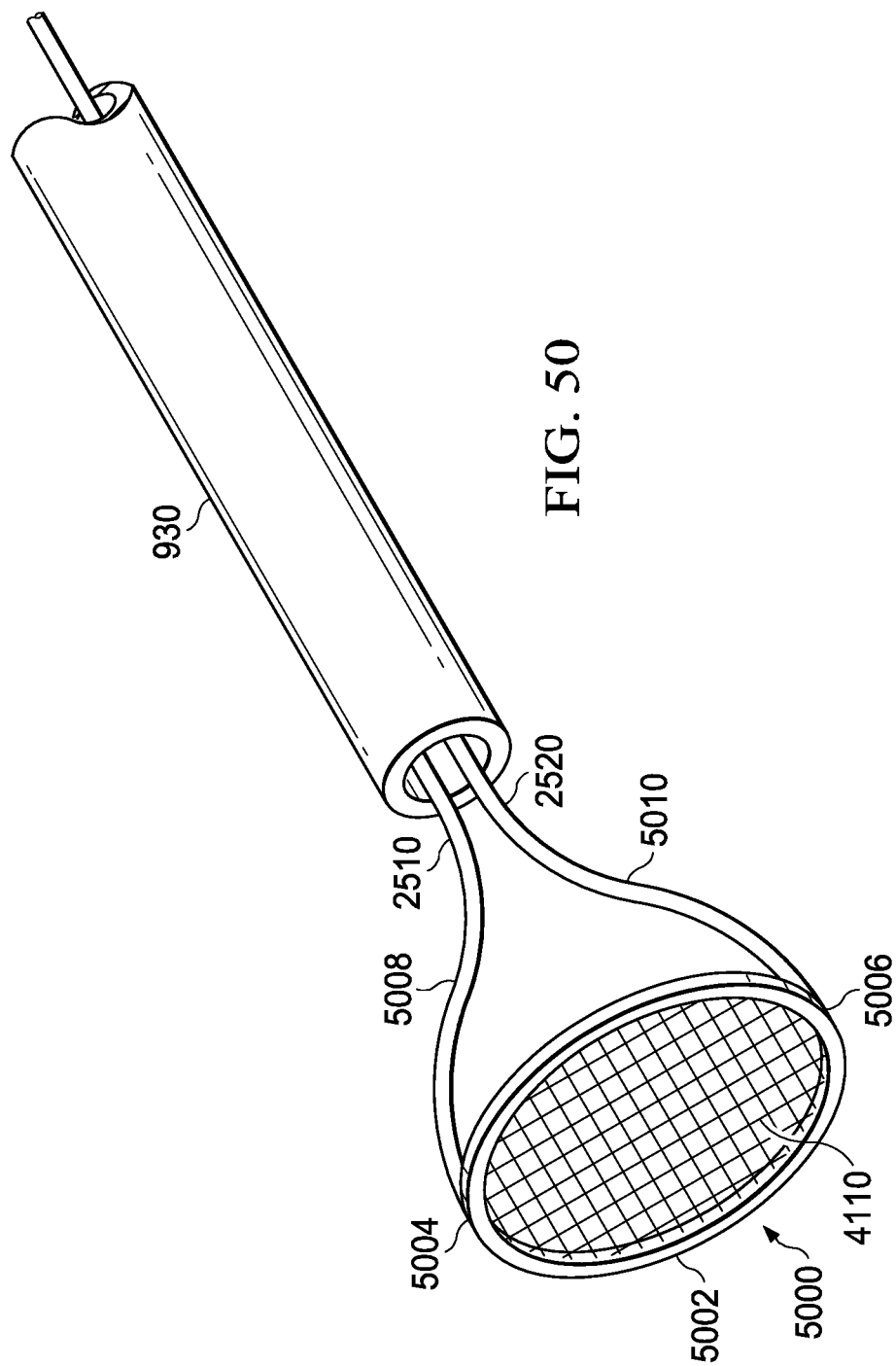
FIGS. 50-53 illustrate an endoscopic stone-extraction device of an embodiment having a circular two-dimensional mesh shape.

FIG. 50 illustrates a circular two-dimensional mesh shape 5000, according to an embodiment. Circular two-dimensional mesh shape 5000 comprises an alternate embodiment of two-dimensional mesh shape 2500. Circular two-dimensional mesh shape 5000 comprises secondary filaments 2510, 2520 coupled to a circular rim 5002 surrounding mesh 4110. According to embodiments, secondary filaments 2510, 2520 are coupled to opposite sides of circular rim 5002 at attachment points 5004, 5006. According to embodiments, attachment points 5004, 5006 are located at opposite sides of rim 5002 so that a line extending from attachment point 5004 to attachment point 5006 bisects circular two-dimensional mesh shape 5000 into two equal halves. Although two attachment points 5004, 5006 are illustrated, embodiments contemplate any number of attachment points 5004, 5006 connecting any number of secondary filaments 2510, 2520 to any locations along circular rim 5002, according to particular needs. According to some embodiments, circular rim 5002 may comprise a rigidity that increases from attachment points 5004, 5006 to the points along the circular rim 5002 halfway between attachment points 5004, 5006. According to other embodiments, the rigidity of circular rim 5002 may decrease from attachment points 5004, 5006 to the points along the circular rim 5002 halfway between attachment points 5004, 5006. By programming the circular rim 5002 with increasing or decreasing rigidity, circular two-dimensional mesh shape 5000 may be configured to open and close by folding substantially along a line bisecting the circular two-dimensional mesh shape 5000 from attachment points 5004, 5006 or along a line perpendicular to it in response to movement of sheath 930 against hips 5008, 5010. According to some embodiments, programming the circular rim 5002 with increasing or decreasing rigidity causes circular two-dimensional mesh shape 5000 to open and close in a convex or concave lens shape. Although circular two-dimensional mesh shape 5000 is illustrated as a circle, embodiments contemplate any type of elliptical shape, according to particular needs.

Figure 51:
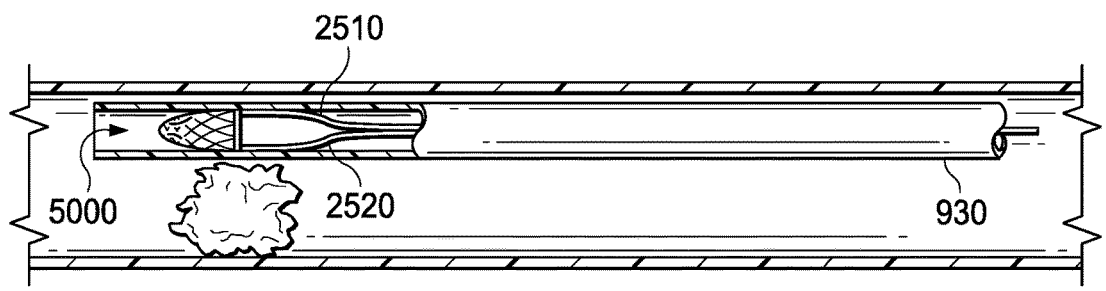

FIG. 51 illustrates circular two-dimensional mesh shape 5000 collapsed in a concave lens shape, according to an embodiment. According to embodiments, using exactly two secondary filaments 2510, 2520 achieves the illustrated concave lens shape of circular two-dimensional mesh shape 5000 when circular two-dimensional mesh shape 5000 partially collapses inside the lumen of sheath 930. The collapsing of circular two-dimensional mesh shape 5000 is caused by a force that is translated from the pressure of sheath 930 pressing against secondary filaments 2510, 2520 as sheath 930 advances along the length of the secondary filaments 2510, 2520. By attaching exactly two secondary filaments 2510, 2520, each on opposite sides of circular two-dimensional mesh shape 5000 at opposite sides or circular rim 5002, circular two-dimensional mesh shape 5000 is free to collapse in a concave lens shape without being restricted by additional secondary filaments. According to embodiments, circular two-dimensional mesh shape 5000 made from a memory material causes circular two-dimensional mesh shape 5000 to collapse in a particular form based on the pressure from sheath 930 against the sides of hips 5008, 5010.

Figure 52:
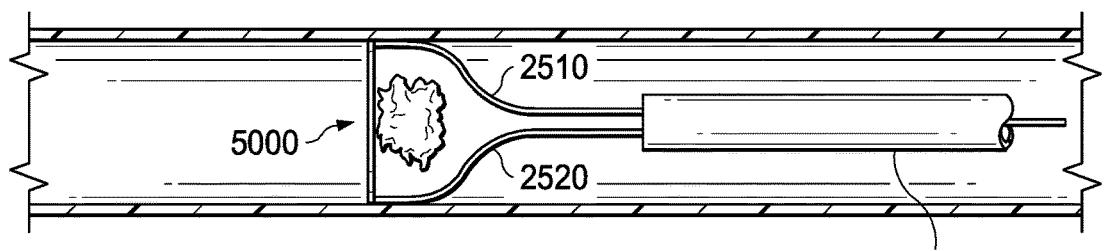

FIG. 52 illustrates circular two-dimensional mesh shape 5000 deployed behind a stone, according to an embodiment. When sheath 930 is retracted, circular two-dimensional mesh shape 5000 opens to form a backstop and stone-capture device to allow stone to be broken up without large fragments being allowed to migrate further up the lumen of, for example, a ureter.

Figure 53:
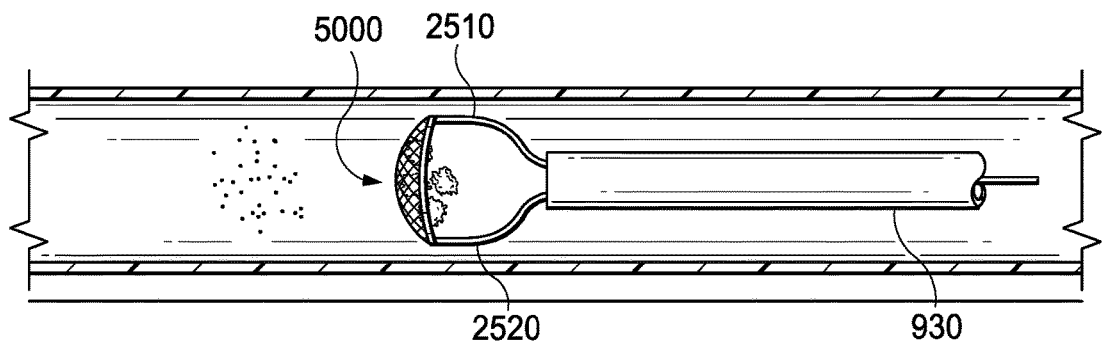

FIG. 53 illustrates circular two-dimensional mesh shape 5000 capturing fragments of a stone while allowing dust to freely pass through, according to an embodiment. While the stone is dusted, such as by a laser, circular two-dimensional mesh shape 5000 captures fragments of the stone which are larger than the openings in mesh 4110 to prevent migration of large fragments while smaller particles of stone dust freely passes through carried by, for example, irrigation. As sheath 930 is advanced, circular two-dimensional mesh shape 5000 partially closes in concave lens shape, which captures most or all of the fragments for removal from the lumen.

Figure 54:
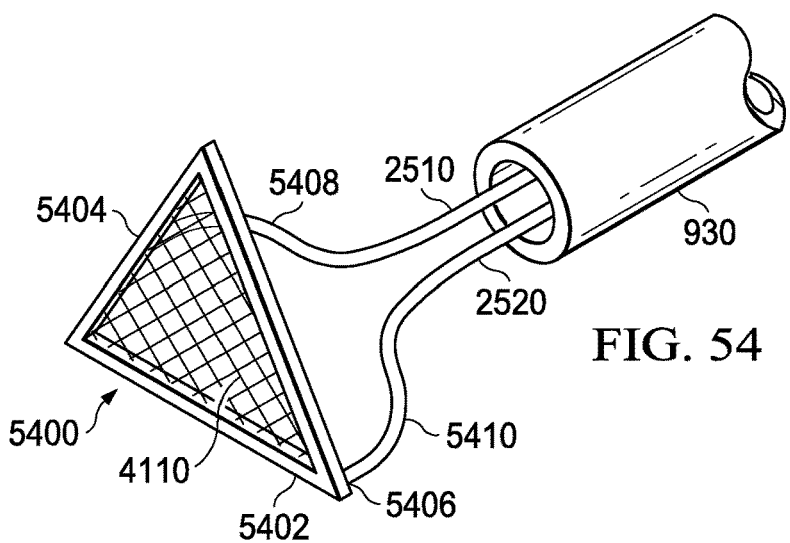
FIGS. 54-56 illustrate an endoscopic stone-extraction device of an embodiment having a triangular two-dimensional mesh shape.

FIG. 54 illustrates a two-dimensional mesh shape when the two-dimensional mesh shape is a triangle, according to an embodiment. Triangular two-dimensional mesh shape 5400 comprises secondary filaments 2510, 2520 coupled to triangular rim 5402. According to embodiments, secondary filaments 2510, 2520 are coupled to opposite sides of triangular rim 5402 at attachment points 5404, 5406. According to embodiments, attachment points 5404, 5406 are located along triangular rim 5402 so that a line extending from attachment point 5404 to attachment point 5406 bisects the triangular mesh shape into two equal halves. For example, attachment point 5404 may comprise the midpoint of a first leg of a triangle and attachment point 5406 may comprise the vertex connecting the second and third legs of the triangle. Although the triangular two-dimensional mesh shape 5400 is depicted as an equilateral triangle, embodiments contemplate any suitable triangular shape with legs of any particular length, according to particular needs. Although two attachment points 5404, 5406 are illustrated, embodiments contemplate any number of attachment points 5404, 5406 connecting any number of secondary filaments 2510, 2520 to any locations along triangular rim 5402, according to particular needs.

According to some embodiments, triangular rim 5402 may comprise a rigidity that increases from attachment points 5404, 5406 to the points along the triangular rim 5402 halfway between attachment points 5404, 5406. According to other embodiments, the rigidity of triangular rim 5402 may decrease from attachment points 5404, 5406 to the points along the triangular rim 5402 halfway between attachment points 5404, 5406. By programming the triangular rim 5402 with increasing or decreasing rigidity, triangular two-dimensional mesh shape 5400 may be configured to open and close by folding substantially along a line bisecting the triangular two-dimensional mesh shape 5400 from attachment points 5404, 5406 or along a line perpendicular to it in response to movement of sheath 930 against hips 5408, 5410. According to some embodiments, programming the triangular rim 5403 with increasing or decreasing rigidity causes triangular two-dimensional mesh shape 5400 to open and close in a convex or concave shape.

Figure 55:
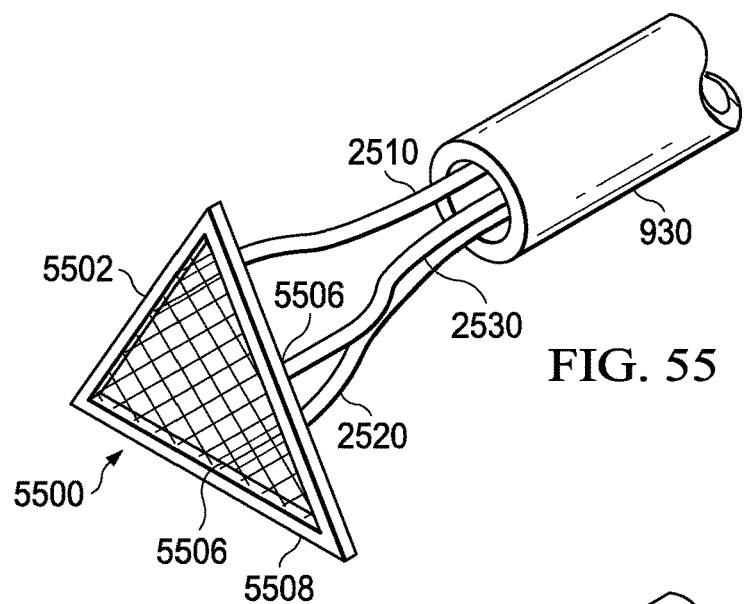

FIG. 55 illustrates a triangular two-dimensional mesh shape 5500 according to a second embodiment. According to embodiments, triangular two-dimensional mesh shape 5500 comprises three attachment points 5502-5506, each connected to one of secondary filaments 2510-2530. According to embodiments, attachment points 5502-5506 are defined by the midpoint of each leg of triangular rim 5508 of triangular two-dimensional mesh shape 5500. Although the triangular two-dimensional mesh shape 5500 is depicted as an equilateral triangle, embodiments contemplate any suitable triangular shape with legs of any particular length, according to particular needs. Although three attachment points 5502-5506 are illustrated, embodiments contemplate any number of attachment points 5502-5506 connecting any number of secondary filaments 2510-2530 to any locations along triangular rim 5502, such as, for example, at each vertex of triangular rim 5502, according to particular needs.

Figure 56:
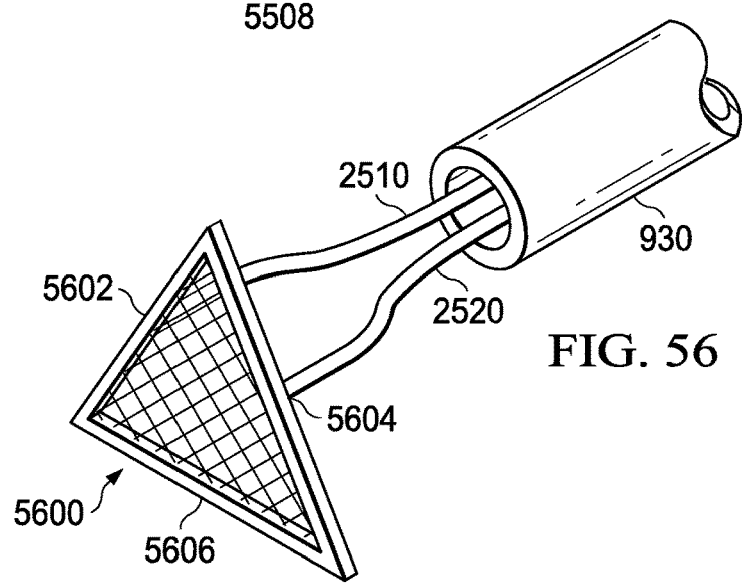

FIG. 56 illustrates a triangular two-dimensional mesh shape according to a third embodiment. According to embodiments, triangular two-dimensional mesh shape 5600 comprises two attachment points 5602, 5604, each connected to one of secondary filaments 2510, 2520. According to embodiments, attachment points 5602, 5604 are defined by the midpoint of two adjacent legs of triangular rim 5606 of triangular two-dimensional mesh shape 5600. Although triangular two-dimensional mesh shape 5600 is depicted as an equilateral triangle, embodiments contemplate any suitable triangular shape with legs of any particular length, according to particular needs.

Regarding construction, the shapes can be formed from a plurality of individual filaments, all of which are joined (e.g., welded, soldered, swaged or otherwise held in place) to the support filament, or the shapes can be formed from a single filament. That single filament can be the support filament or can be a filament that is separate from but joined to the support filament. Further, shapes can be made from a shape memory material such as shape memory metal, such as nitinol, although other materials can be used. In one embodiment, the shape is made from preferably small, flexible, kink-resistant wires that are capable of collapsing together to fit within the lumen.

Also, the shapes can be sized in any suitable fashion. For example, in one embodiment, the opening of the shape can be sized to admit a stone that is at least two millimeters in diameter (or less) or as large as 5 mm (or more) in diameter. Of course, other sizes and ranges can be used.

Exemplary Handles

Figure 46:
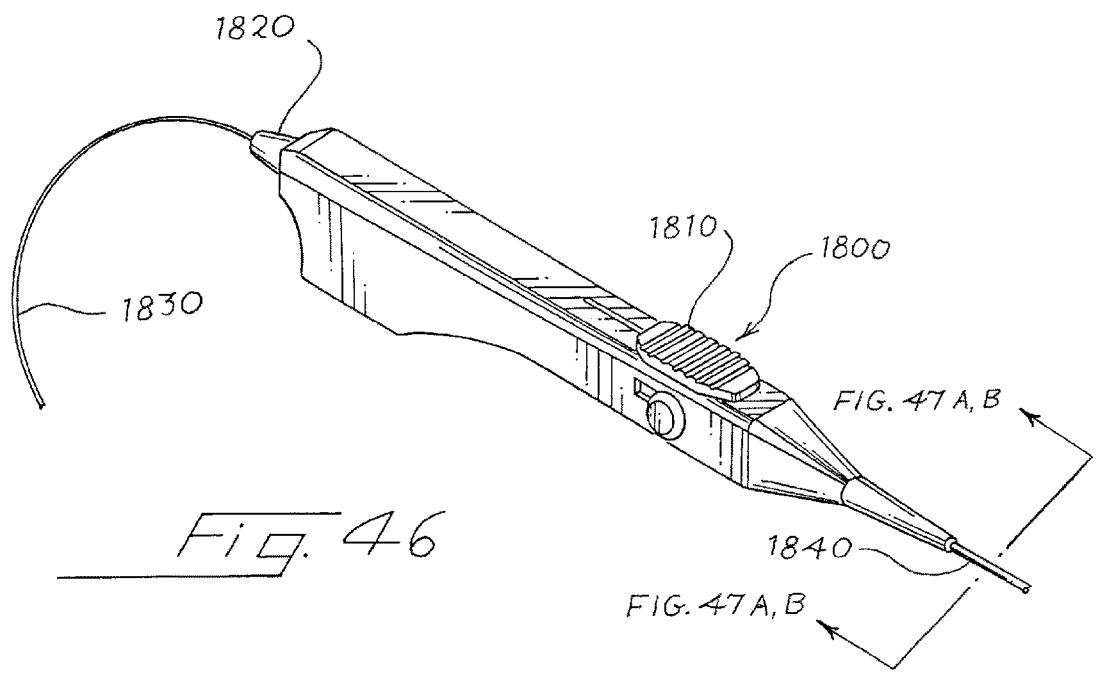
FIG. 46 illustrates a handle of an endoscopic stone-extraction device of an embodiment, wherein the handle has a laser fiber entry port.
Figure 47A:
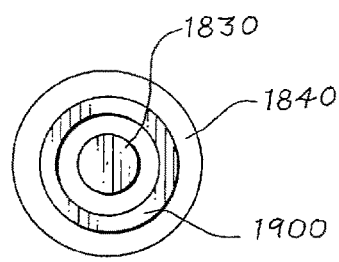
FIG. 47A illustrates a cross-section of a sheath of an embodiment where a laser fiber is internal to a stone-extraction filament.
Figure 47B:
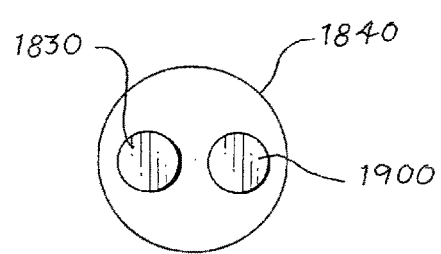
FIG. 47B illustrates a cross-section of a sheath of an embodiment where a laser fiber is external to a stone-extraction filament.

As noted above, any type of handle can be used with the stone-extraction devices of these embodiments. For example, the handle 1700 can simply be a device with an actuator 1710 to deploy the plurality of loops (as in FIG. 45). In another embodiment (see FIG. 46), the handle 1800 not only has an actuator 1810, but also has a port 1820 for a laser fiber 1830. (The omniFORCE™ Laser Stone Cage by Omnitech Systems is an example of such a handle.) As shown in FIGS. 47A and 47B, the laser fiber 1830 can either be internal to (FIG. 47A) or external to (FIG. 47B) the filament 1900, 1910 within the sheath 1840. The advantage of using this type of handle 1800 is that the ureteroscope does not need to be removed and reinserted into the body in order to provide a free port for the laser fiber, as the laser fiber is already provided in the sheath 1840. Another way of obtaining this advantage of not removing the scope is by using a Y-adaptor 2100 (see FIG. 49) that would fit on one of the ports 220 of the scope 200, allowing both the stone-extraction sheath and the laser fiber to use the same port 220 on the scope 200. (The Y-adaptor used with the Escape® Basket from Boston Scientific is an exemplary adaptor.) In this alternative, it is preferred that the sheath and the laser fiber be sized so that they can both fit together inside the port 220.

As mentioned above, other handle designs can be used. The following paragraphs and drawings describe yet another handle design. Again, this and the other handle designs described herein are merely examples and should not be read into the claims.

Figure 1:
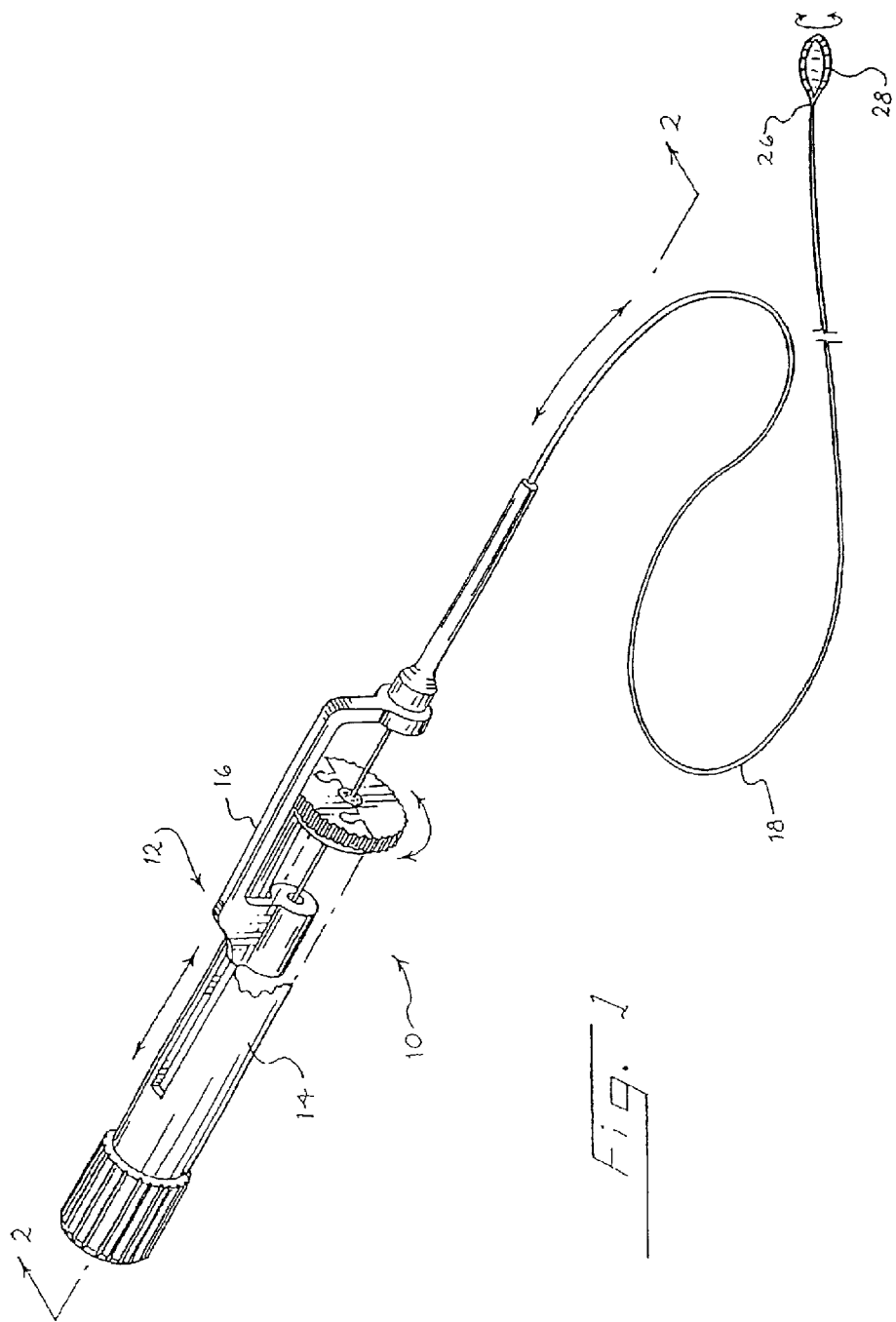
FIG. 1 illustrates perspective view of an endoscopic stone extraction device of an embodiment.
Figure 13:
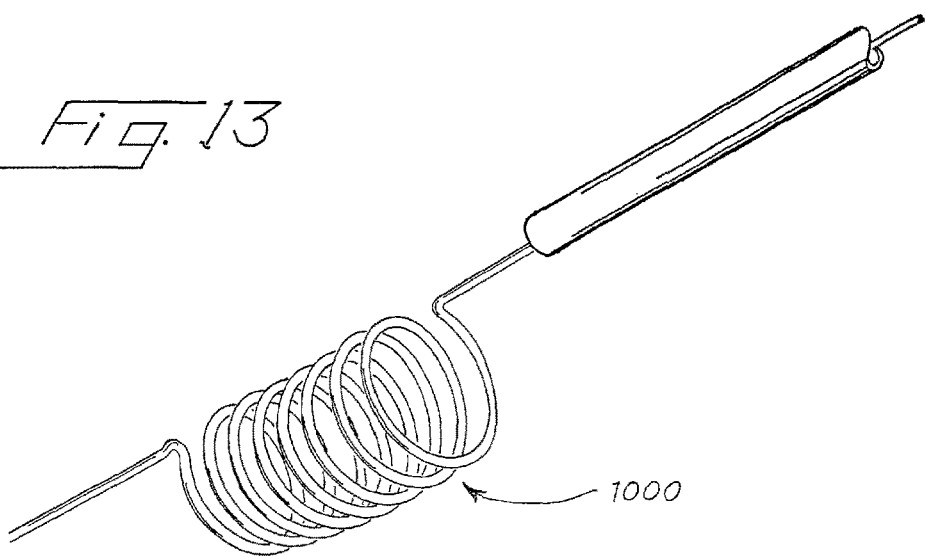
FIGS. 13-16 illustrate an endoscopic stone-extraction device of an embodiment having a non-tapered corkscrew shape.
Figure 14:
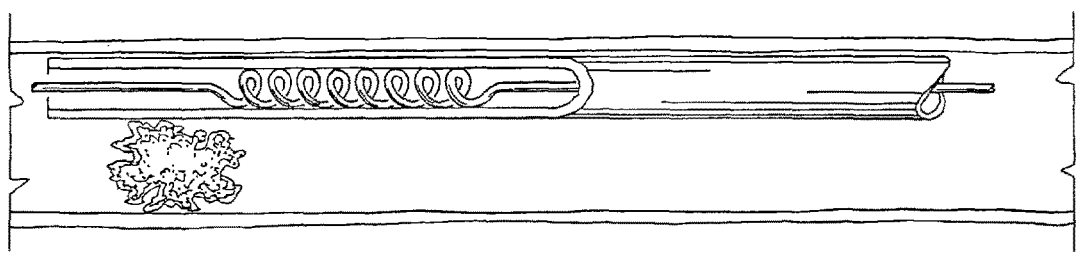
Figure 15:
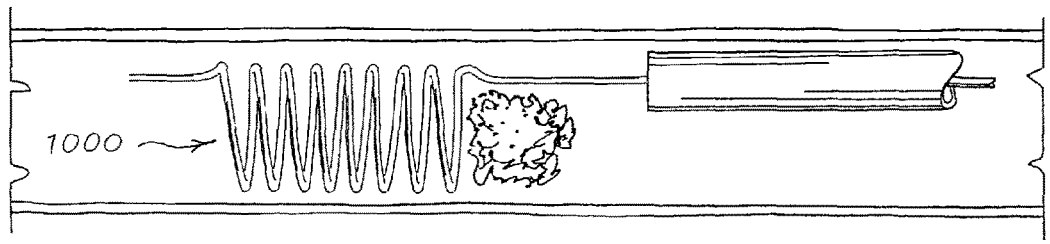
Figure 16:
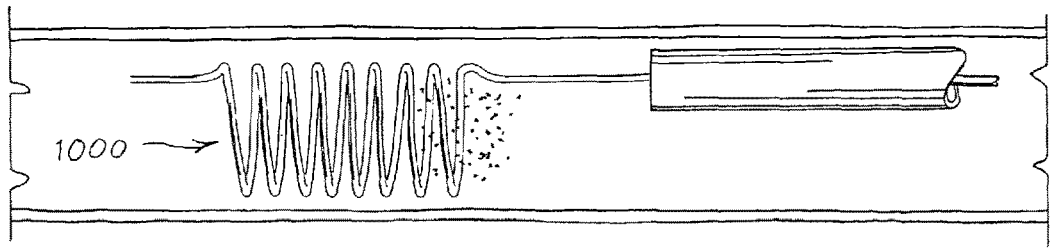
Figure 21:
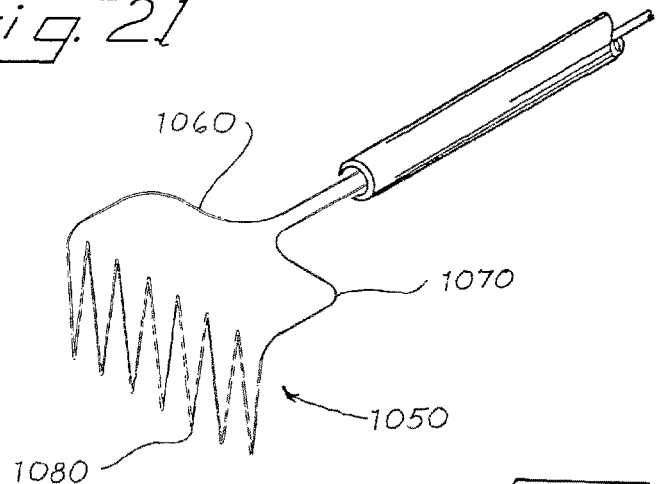
FIGS. 21-24 illustrate an endoscopic stone-extraction device of an embodiment having a rake shape.
Figure 22:
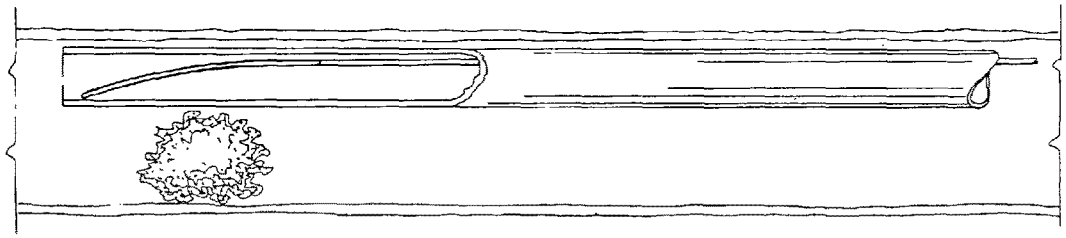
Figure 23:
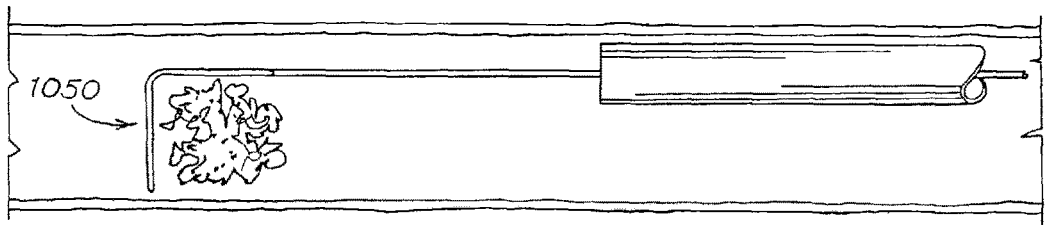
Figure 24:
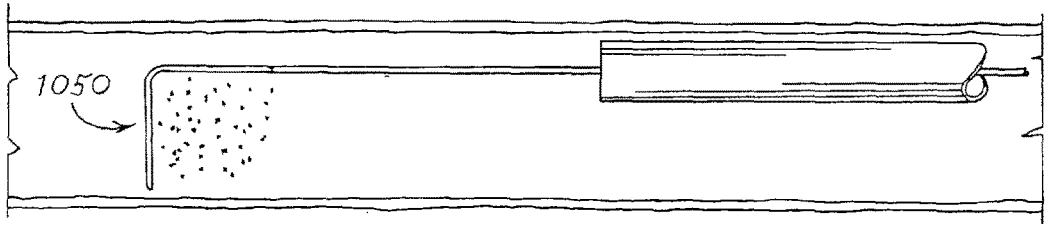
Figure 25:
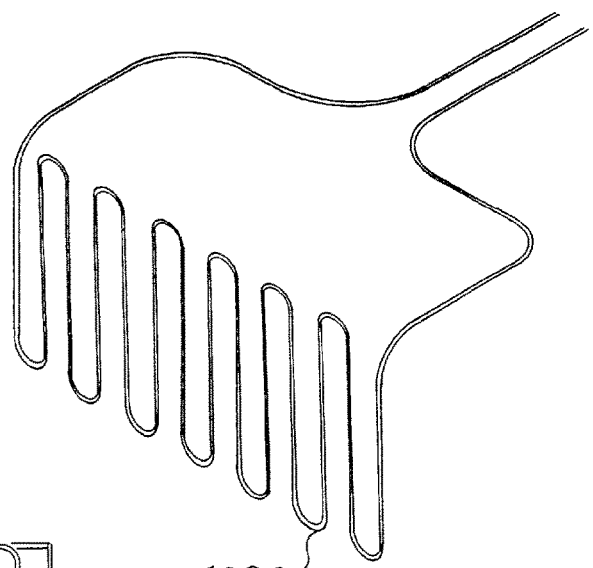
FIGS. 25-26 illustrate an alternate rake shape of an embodiment.
Figure 26:
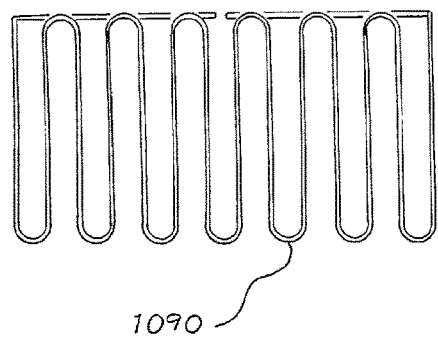
Figure 31:
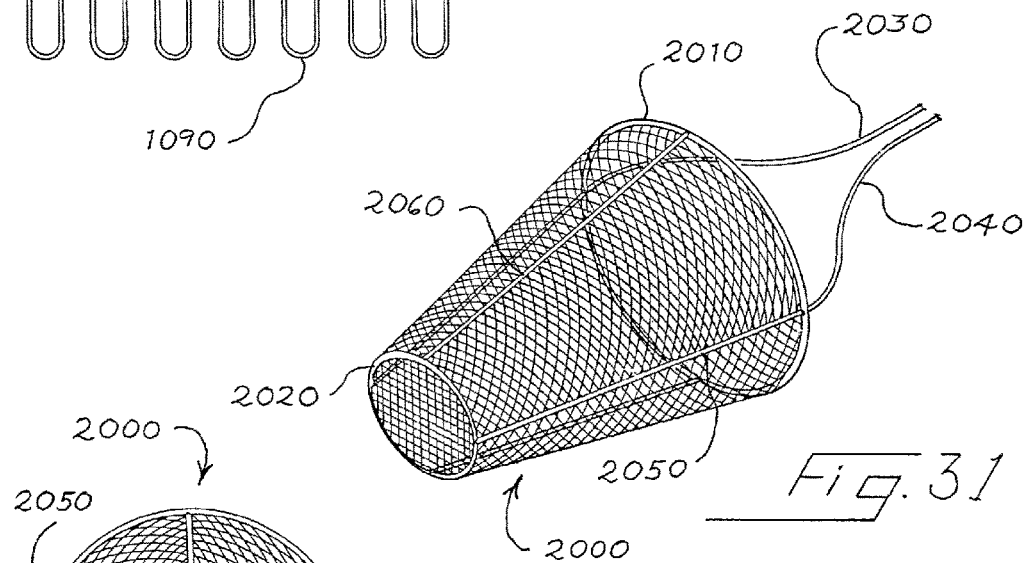
FIGS. 31-32 illustrate an endoscopic stone-extraction device of an embodiment having a meshed basket, circular shape.
Figure 32:
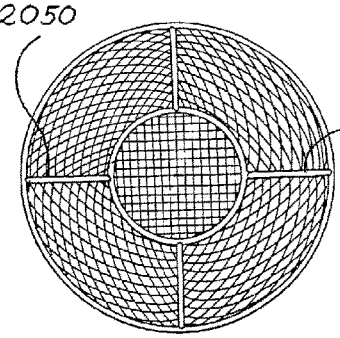
Figure 33:
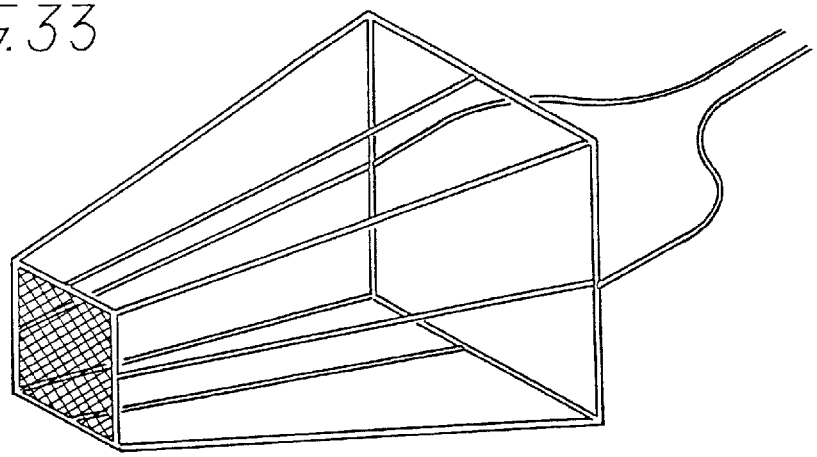
FIGS. 33-36 illustrate an endoscopic stone-extraction device of an embodiment having an open and closed basket, rectangular shapes.
Figure 34:
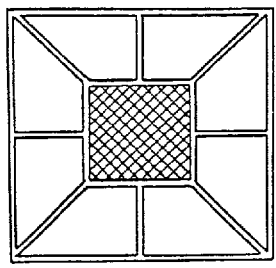
Figure 35:
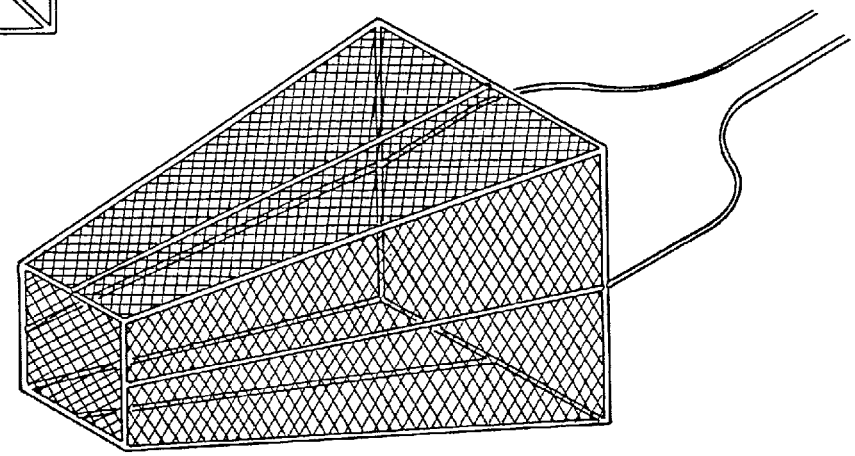
Figure 36:
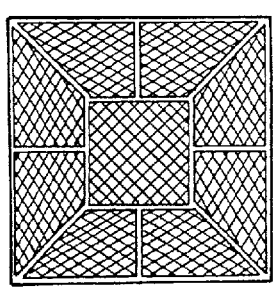

Returning to the drawings, FIG. 1 shows an endoscopic stone extraction device 10 of an embodiment. The device 10 includes a handle 12 that in turn includes a grip 14 and a slide 16. As explained in greater detail below, the slide 16 is mounted to slide longitudinally along the length of the grip 14.

A tubular sheath 18 is secured to the slide 16. The sheath 18 defines a lumen 19, and the sheath 18 can be formed of any suitable flexible material. A strain relief collar 20 is provided at the point where the sheath 18 is secured to the slide 16 to reduce the incidence of kinking.

The device also includes a filament 22 having a first end 24 (FIG. 2) and a second end 26 (FIG. 1). The first end 24 is rotatably secured to the grip 14 (FIG. 2), and the second end 26 supports a stone extraction basket (this basket is of a different shape than the stone-extraction device discussed above, as this handle can be used with a variety of baskets). The filament 22 can be formed of any suitable material, and is typically formed of a flexible metallic wire. Preferably, the first end 24 is thicker and stiffer than the second end 26 to facilitate insertion and manipulation of the basket 28.

The following sections will first describe the handle 12 in greater detail.

As best shown in FIG. 2, the handle 12 includes a tube 30 that defines a longitudinally extending slot 32. The tube 30 forms a bore 34 and terminates at one end in external threads 36. Protruding elements 38 extend away from the perimeter of the tube 30 to facilitate the grasping of the tube 30 by a physician during use. For purposes of discussion, the portion of the tube 30 adjacent the external threads 36 will be referred to as the rear portion 42, and the opposite end of the tube 30 will be referred to as the front portion 40. The tube 30 may for example be formed of any suitable, moldable thermoplastic material, though the widest variety of materials can be adapted for use.

Continuing with FIG. 2, the slide 16 includes a guide cylinder 50 sized to slide along the bore 34 of the tube 30. This guide cylinder 50 defines a central opening 52 sized to pass the filament 22 with little or no friction therebetween. The slide 16 also includes an arm 54 that extends from the guide cylinder 50 through the slot 32 to a plate 56. The arm 54 holds the plate 56 in alignment with the centerline of the tube 30. The slide 16 includes a gripping portion 58 that can be pushed or pulled by a physician during use to move the slide 16 along the longitudinal axis of the tube 30. As before, a wide range of materials can be used for the slide 16, including any suitable thermoplastic material.

As shown in FIGS. 1-5, a disk 60 is provided. This disk 60 is positioned adjacent the front portion 40 of the tube 30. The disk 60 is clamped onto the filament 22, and the disk 60 is rotatable with respect to both the tube 30 and the slide 16. As shown in FIGS. 3-5, the disk 60 includes half-disks 66, 68 that snap together in a releasable manner. The half-disks 66, 68 carry respective elastomeric gripping portions 69 designed to grip the filament 22 therebetween when the half-disks 66, 67 are snapped together.

As best shown in FIGS. 1, 2, 6 and 6A, the handle 12 carries a threaded cap 70 that defines a set of internal threads sized to mate with the external threads 36. The cap 70 includes a socket 71 that bears on a chuck 72. When the cap 70 is tightened in place, the chuck 72 is held between the socket 71 and an internal socket 31 formed by the tube 30. The chuck 72 is free to rotate but not to translate with respect to the tube 30.

The chuck 72 includes two parts 73, each having a central groove 77 sized to clamp against the filament 22. The groove 77 may be lined with an elastometric layer to ensure good frictional contact between the chuck 72 and the filament 22. Each part 73 defines external threads, and the parts 73 are clamped against the filament by a cap nut 74 such that the chuck 72 rotates and translates in unison with the filament 22. The chuck 72 forms a convex surface 75 that engages the socket 31, and a convex surface 76 that engages the socket 71. The surfaces 75, 76 are shaped to allow low-friction rotation of the chuck 72 and the filament 22 relative to the tube 30. Thus, the chuck 72 and associated elements carried by the tube 30 form a rotational joint. Other types of rotational joints may be used, including ball-and-socket joints. For example, a ball-and-socket joint may be included in the filament 22 near the first end 24, and the first end 24 may be fixed to the tube 30. Also, the filament may have an enlarged end that forms part of the rotational joint, and the enlarged end may be sized to fit through the lumen of the sheath 18. Alternatively, the enlarged end may be too large to fit through the lumen of the sheath, and may be removable from the body of the filament 22, e.g. by disassembling the enlarged end from the filament 22.

In use, the device 10 is assembled as shown in FIGS. 1 and 2. Initially, the slide 16 is advanced (i.e. moved to the right in the view of FIG. 2) to move the sheath 18 over the basket 28. This reduces the cross-sectional dimensions of the basket 28 and facilitates insertion of the basket 28 into a region of the body adjacent to the stone to be removed. The slide 16 is then moved to the left in the view of FIG. 2 to expose the basket 28, which resiliently assumes an enlarged operational shape.

It should be apparent from the foregoing discussion that rotation of the disk 60 and the filament 22 occurs without rotation of the sheath 18, the slide 16 or the handle 12. This arrangement facilitates rotation of the filament 22 and the basket 28 inside the lumen of the body cavity in which it is inserted, since friction between the sheath 18 and the endoscopic device and between the sheath 18 and adjacent tissue do not impede rotation of the filament 22 and the basket 28. Rotation of the filament 22 is guided by the rotational joint that includes the chuck 72. Once a stone has been captured within the basket, the slide 16 is then moved to the right in the view of FIG. 2 to move the sheath over at least a portion of the basket, thereby securely capturing the stone in the basket for removal.

On occasion, it may be necessary to remove the handle 12, the slide 16 and the sheath 18 while leaving the filament 22 and the basket 28 in place. This can readily be accomplished by unscrewing the cap 70 from the handle 12, removing the cap nut 74 from the parts 73, and then removing the parts 73, handle 12, slide 16 and sheath 18 from the filament 22.

The disk 60 is an example of a manipulator used to rotate the filament 22 relative to the handle 12. This manipulator can take other forms, including the form shown in FIGS. 7 and 8. The embodiment of FIGS. 7 and 8 is similar to that of FIGS. 1 and 2, except that the disk 60 has been replaced by a lever 80. This lever 80 defines a free end 82 and hinged end 84, and the free end 82 is positioned closer to the first end 24 of the filament 22 than is the hinged end 84. During normal use, the lever 80 is positioned as shown in FIG. 7 in an extended position. In this position the user can apply torques to the lever 80 and therefore to the filament 22 to rotate the filament 22 as described above. The hinged end 84 is connected to the filament 22 at a hinged joint (e.g. a living hinge or a multiple-part hinge) and the lever 80 can be moved to the retracted position shown in dotted lines in FIG. 8. In this retracted position, the lever 80 can be moved through the lumen of the sheath 18, thereby allowing the handle, slide and sheath to be removed from the filament 22 as described above.

CONCLUSION

It should be apparent from the foregoing detailed description that improved endoscopic stone extraction devices have been described that are well suited to the collection of a wide variety of stones, including stone fragments. The baskets described above are well suited for the removal of many types of debris, including for example, stones, stone fragments, and cholesterol plaque fragments. The devices described above can be used with the widest variety of endoscopes, including ureteroscopes, nephroscopes and other endoscopic devices, and they can be used within the lumens of many body tissues, including for example, ureters, bile ducts, and blood vessels.

As used herein, the term "stone" is intended broadly to encompass a wide variety of biological stones, calculus and the like, including fragments of stones, calculus and the like formed by any of the techniques described above or other techniques developed in the future. Urinary tract stones and biliary tract stones are two examples.

The term "end portion" is intended broadly to encompass the end of structure such as a filament along with an adjacent portion of the structure.

The term "surface" is intended broadly to encompass perforated surfaces. The term "filament" is intended broadly to encompass wires and other elongated structures formed of any of a wide range of materials, including metals, plastics, and other polymers.

Also, any of the embodiments in the following documents, which are hereby incorporated by reference, can be used in combination with the embodiments discussed herein: U.S. Pat. Nos. 6,743,237; 7,087,062; 6,419,679; 6,494,885; 6,551,327; and U.S. patent application Ser. No. 13/963,780.

The foregoing detailed description has discussed only a few of the many forms that this invention can take. For this reason, this detailed description is intended by way of illustration and not limitation. It is only the following claims, including all equivalents, that are intended to define the scope of this invention.

What is claimed is:

1. An endoscopic stone-extraction device comprising:
   a support filament comprising an end portion;
   a sheath comprising a lumen, wherein the support filament is disposed in the lumen such that the sheath is slideable with respect to the support filament; and
   a laser fiber disposed within the sheath;
   wherein movement of an actuator in a first direction retracts the sheath and causes the end portion to expand outside the lumen in a two-dimensional mesh shape that is generally perpendicular to an axis of the lumen;
   wherein the two-dimensional mesh shape is made of a shape memory material and is connected to the support filament via two secondary filaments;
   wherein the two secondary filaments attach on two opposite sides of the two-dimensional mesh shape and comprises a rim with a rigidity that increases with distance from an attachment point to a point halfway between the attachment point and a second attachment point; and
   wherein movement of the actuator in a second direction advances the sheath and causes the two-dimensional mesh shape to at least partially collapse inside the lumen.

2. The endoscopic stone-extraction device of claim 1, wherein the laser fiber fits alongside the support filament.

3. The endoscopic stone-extraction device of claim 1, wherein the laser fiber is disposed within the support filament.

4. The endoscopic stone-extraction device of claim 1, wherein the shape memory material comprises a shape memory metal.

5. The endoscopic stone-extraction device of claim 1, wherein the two-dimensional mesh shape is configured to extract a stone and configured to serve as a mechanical trapping/backstop device.

6. The endoscopic stone-extraction device of claim 1, wherein the two-dimensional mesh shape is formed from a plurality of filaments.

7. The endoscopic stone-extraction device of claim 1, wherein the two-dimensional mesh shape is selected from the following shapes: a square, a circle, and a triangle.

8. The endoscopic stone-extraction device of claim 1, wherein the two-dimensional mesh shape is a polygon.

9. An endoscopic stone-extraction device comprising:
a support filament comprising an end portion;
a sheath comprising a lumen, wherein the support filament is disposed in the lumen such that the sheath is slideable with respect to the support filament;
a handle comprising an actuator and a laser fiber port; and
a laser fiber disposed within the sheath;
wherein the end portion comprises a two-dimensional mesh shape and comprises a shape memory material that expands outside the lumen to trap a stone and to serve as a mechanical backstop to prevent migration of a stone;
wherein the two-dimensional mesh shape is generally perpendicular to an axis of the lumen, the two-dimensional mesh shape is connected to the support filament via two secondary filaments coupled to opposite sides of the two-dimensional mesh shape; and
wherein the two-dimensional mesh shape is configured to collapse inside the lumen of the sheath and comprises a rim with a rigidity that increases with distance from an attachment point to a point halfway between the attachment point and a second attachment point.

10. The endoscopic stone-extraction device of claim 9, wherein the laser fiber fits alongside the support filament.

11. The endoscopic stone-extraction device of claim 9, wherein the laser fiber is disposed within the support filament.

12. The endoscopic stone-extraction device of claim 9, wherein the two-dimensional shape is formed from a plurality of filaments.

13. The endoscopic stone-extraction device of claim 9, wherein the shape memory material comprises a shape memory metal.

14. The endoscopic stone-extraction device of claim 9, wherein the two-dimensional mesh shape is selected from the following shapes: a square, a circle, and a triangle.

15. The endoscopic stone-extraction device of claim 9, wherein the two-dimensional mesh shape is a polygon.

16. An endoscopic stone-extraction device comprising:
a support filament comprising an end portion;
a sheath comprising a lumen, wherein the support filament is disposed in the lumen such that the sheath is slideable with respect to the support filament;
a handle comprising an actuator and a laser fiber port; and
a laser fiber disposed within the sheath;
wherein the end portion comprises a two-dimensional mesh shape and comprises a shape memory material that expands outside the lumen to trap a stone and to serve as a mechanical backstop to prevent migration of a stone;
wherein the two-dimensional mesh shape is generally perpendicular to an axis of the lumen, the two-dimensional mesh shape is connected to the support filament via two secondary filaments coupled to opposite sides of the two-dimensional mesh shape; and
wherein the two-dimensional mesh shape is configured to collapse inside the lumen of the sheath and comprises a rim that is softer than a mesh disposed within the rim.

* * * * *